(12) United States Patent
Johal et al.

(10) Patent No.: US 6,750,380 B1
(45) Date of Patent: Jun. 15, 2004

(54) ISOLATED NUCLEIC ACID MOELCULES ENCODING THE DW3 P-GLYCOPROTEIN OF SORGHUM AND METHODS OF MODIFYING GROWTH IN TRANSGENIC PLANTS THEREWITH

(75) Inventors: Gurmukh S. Johal, Urbandale, IA (US); Dilbag S. Multani, Johnston, IA (US)

(73) Assignees: Pioneer Hi-Bred International, Inc., Des Moines, IA (US); The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 09/711,619

(22) Filed: Nov. 13, 2000

Related U.S. Application Data
(60) Provisional application No. 60/165,176, filed on Nov. 12, 1999.

(51) Int. Cl.$^7$ .................. C12N 15/29; C12N 15/82; A01H 5/00; A01H 5/10
(52) U.S. Cl. ................ 800/298; 435/320.1; 435/419; 536/23.6; 800/320; 800/320.1; 800/320.2; 800/312; 800/290; 800/289
(58) Field of Search .............. 536/23.1, 23.6; 435/320.1, 468, 419; 800/278, 289, 287, 290, 298, 309, 312, 314, 322, 320.1, 320.2, 320.3, 320

(56) References Cited

U.S. PATENT DOCUMENTS

2002/0162142 A1   10/2002   Johal et al. ............... 800/290

OTHER PUBLICATIONS

Colliver et al., Differential modification of flavonoid and isoflavonoid biosynthesis with an antisens chalcone synthase construct in transgenic Lotus corniculatus, 1997, Plant Molecular Biology, vol. 35, pp. 509–522.*
Dudler et al., Sturcture of an mdr–like Gene from Arabidopsis thaliana, 1992, The Journal of Biological Chemistry, vol. 267, No. 9, pp. 5882–5888.*
Wang et al., A potato cDNA encoding a homologue of mammalian multudrug resistant P–glycoprotein, 1996, Plant Molecular Biology, vol. 31, pp. 683–687.*
Sidler et al., Involvement of an ABC Transporter in a Developmental Pathway Regulating Hypocotyl Cell Elongation in the Light, Oct. 1998, The Plant Cell, vol. 10, pp. 1623–1636.*
Bowie et al 1990, Science 247:1306–1310.*
Fourgoux–Nicol et al 1999, Plant Molecular Biology 40:857–872.*
Hill et al 1998, Biochemical and Biophysical Research Communications 244:573–577.*
Lazar et al 1988, Molecular and Cellular Biology 8(3):1247–1252.*
Broun et al 1998, Science 282:1315–1317.*
Bennetzen, et al. "Molecular cloning of maize genes by transposon tagging with *Mulator*" Plant Gene Systems and Their Biology, (1987), pp. 183–204, University of California Los Angeles.
Campbell, et al. "Effects of a single height gene dw–3 of sorghum on certain agronomic characters" Crop Science, (1975), pp. 595–597, vol. 15 (4).
Davies, et al.. "Cloning and characterization of a novel P–glycoprotein homologue from barley", Gene, pp. 195–202, vol. 199(1–2), Amsterdam.
Dudler, et al. "Structure of an MDR–like gene from arabidopsis–thaliana evolutionary implications", Journal of Biological Chemistry, (1992) pp. 5882–5888, vol. 267(9).
Fleenor, et al. "Nucleotide sequence of the maize mutator element mu8", Nucleic Acids Research, (1990) vol. 18 (22), p. 6725.
Spray, et al. "Cloning a maize dwarfing gene by transposon tagging", Plant Physiology (1995) vol. 108 (2) Supp., p. 132, Annual Meeting of the American Society Plant Physiologists, Charlotte, North Carolina, USA.
Wang, et al. "A potato cDNA encoding a homologue of mammalian multidrug resistant P–glycoprotein", Plant Molecular Biology, (1996) pp. 683–687, vol. 31 (3).
Chen et al., Genbank Accession No. P08183, Nov. 1, 1997.
Davies et al., Genbank Accession No. Y10099, Oct. 24, 1997.
Davies, T.G.E., Genbank Accession No. CAA71179, Oct. 24, 1997.
Dudler et al., Genbank Accession No. A42150, Mar. 13, 1997.
Dudler et al., Genbank Accession No. X61370, Nov. 9, 1998.
Marques, J.P., Genbank Accession No. Y10227, May 19, 1997.
Marques, J.P., Genbank Accession No. Y10228, May 19, 1997.
Sidler et al., Genbank Accession No. Y15990, Dec. 28, 1997.
Sidler et al., Involvement of an ABC Transporter in a Developmental Pathway Regulating Hypocotyl Cell Elongation in the Light, *The Plant Cell*, Oct. 1998, pp. 1623–1636, vol. 10, American Society of Plant Physiologists.

(List continued on next page.)

*Primary Examiner*—Amy J. Nelson
*Assistant Examiner*—David H Kruse
(74) *Attorney, Agent, or Firm*—Alston & Bird LLP

(57) ABSTRACT

The invention relates to the genetic modification of plants particularly to the expression of P-glycoprotein genes in transformed plants. Nucleotide sequences for Dw3 genes encoding a P-glycoprotein of sorghum, and method for their use are provided. The sequences fine use in modifying the growth of plants. Additionally, the invention provides methods for producing stable dwarf crop plants, particularly stable dwarf sorghum plants.

23 Claims, No Drawings

OTHER PUBLICATIONS

Smart et al., Hormonal and Environmental Regulation of a Plant PDR5–Like ABC Transporter, *The Journal of Biological Chemistry*, Aug. 1996, pp. 19351–19357, vol. 271 (32), The American Society for Biochemistry and Molecular Biology, Inc., USA.

Wang et al., Genbank Accession No. U52079, Feb. 1, 1999.

Wang et al., Genbank Accession No. AAD10836, Jan. 31, 1999.

* cited by examiner

```
                              SEQUENCE LISTING

<160> NUMBER OF SEQ ID NOS:  9

<210> SEQ ID NO 1
<211> LENGTH: 2139
<212> TYPE: DNA
<213> ORGANISM: Sorghum bicolor

<400> SEQUENCE: 1
ctcctcgccg tgttcccgct cgtcgtgggc gccaccgtgc tgcagaagat gttcatgaag      60
ggcttctcgg gggacctgga ggccgcgcac gccagggcca cgcagatcgc gggcgaggcc     120
gtggccaacc tgcgcaccgt ggccgcgttc aacgcggagc gcaagatcac ggggctgttc     180
gaggccaacc tgcgcggccc gctccggcgc tgcttctgga aggggcagat cgccggcagc     240
ggctacggcg tggcgcagtt cctgctgtac gcgtcctacg cgctggggct gtggtacgcg     300
gcgtggctgg tgaagcacgg cgtgtccgac ttctcgcgca ccatccgcgt gttcatggtg     360
ctgatggtgt ccgccaacgg cgccgccgag acgctgacgc tggcgccgga ctttgtcaag     420
ggcgggcgcg cgatgcggtc cgtgttcgag accatcgacc ggaaaacgga ggtggagccc     480
gacgacgtgg acgcggcgcc ggtgccggag cggcccaagg gcgaggtgga gctgaagcac     540
gtggacttct cgtacccgtc gcggccggac atccaggtgt ccgcgacct gagcctccgg     600 gcgcgcgccg ggaagacgct ggcgctggtg ggtccgagcg ggtgcggcaa gagctcggtg     660
ctggcgctgg cgcagcggtt ctacgagccc acgtccgggc gcgtgctcct ggacggcaag     720
gacgtgcgca agtacaacct gcgggcgctg cggcgcgtgg tggcggtggt gccgcaggag     780
ccgttcctgt tcgcggcgag catccacgac aacatcgcgt acgggcgcga gggcgcgacg     840
gaggcggagg tggtggaggc ggcgactcaa gcgaacgcgc accggttcat ctcggcgctg     900
ccggagggct acgggacgca agtgggcgag cgcggggtgc agctgtcggg cgggcagcgg     960
cagcggatcg cgatcgcgcg cgcgctggtg aagcaagcgg ccatcatgcc gctggacgag    1020
gcgaccagcg cgctggaccc gagtcggagc ggtggctctt cgaggccaac cttcgcggcc    1080
cgctccggcg cttgttctgg aagggcagga tcgcgggaac ggtacgggcg tggcgcagtt    1140
cttgctgacg cgtcctacgc gcttggggtt ttggtacccc gcgtggctag tgaagcacgg    1200
gtctccgact ttcgcgcacc atccgggtgt tcatggtgct gatggtgtcc gccaacggcg    1260
```

-continued

```
ccgccgagac gctgacgctg gcgccggact ttgtcaaggg cgggcgcgcg atgcggtccg    1320
tgttcgagac catcgaccgg aaaacggagg tggagcccga cgacgtggac gcggcgccgg    1380
tgccggagcg gcccaaggc gaggtggagc tgaagcacgt ggacttctcg tacccgtcgc     1440
ggccggacat ccaggtgttc cgcgacctga gcctccgggc gcgcgccggg aagacgctgg    1500
cgctggtggg tccgagcggg tgcggcaaga gctcggtgct ggcgctggtg cagcggttct    1560
acgagcccac gtccgggcgc gtgctcctgg acggcaagga cgtgcgcaag tacaacctgc    1620
gggcgctgcg gcgcgtggtg gcggtggtgc cgcaggagcc gttcctgttc gcggcgagca    1680
tccacgacaa catcgcgtac gggcgcgagg gcgcgacgga gcggaggtg gtggaggcgg     1740 cgacgcaggc gaacgcgcac cggttcatct cggcgctgcc ggagggctac gggacgcagg    1800
tgggcgagcg cggggtgcag ctgtcgggcg ggcagcggca gcggatcgcg atcgcgcgcg    1860
ctggtaagca gcggccatcg tgctgctgga cgaggcgacc agcgcgctgg acgccgagtc    1920
ggagcggtgc gtgcaggagg cgctggagcg cgcggggtcc gggcgcacca ccatcgtggt    1980
ggcgcaccgg ctggccacgg tgcgcggcgc gcacaccatc gcggtcatcg acgacggcaa    2040
ggtggcggag caggggtcgc actcgcacct gctcaagcac catcccgacg ggtgctacgc    2100
gcggatgctg cagctgcagc ggctgacggg cgcggcggc                           2139
```

<210> SEQ ID NO 2
<211> LENGTH: 1267
<212> TYPE: DNA
<213> ORGANISM: Sorghum bicolor

<400> SEQUENCE: 2

```
ctcctcgccg tgttcccgct cgtcgtgggc gccaccgtgc tgcagaagat gttcatgaag    60
ggcttctcgg gggacctgga ggccgcgcac gccagggcca cgcagatcgc gggcgaggcc    120
gtggccaacc tgcgcaccgt ggccgcgttc aacgcggagc gcaagatcac ggggctgttc    180
gaggccaacc tgcgcggccc gctccggcgc tgcttctgga agggcagat cgccggcagc     240 ggctacggcg tggcgcagtt cctgctgtac gcgtcctacg cgctgggcct gtggtacgcg    300
gcgtggctgg tgaagcacgg cgtgtccgac ttctcgcgca ccatccgcgt gttcatggtg    360
ctgatggtgt ccgcgaacgg gcgcccgccg agacgctgac gctggcgccg gacttcatca    420
agggcgggcg cgcgatgcgg tcggtgttcg agacgatcga ccgcaagacg gaggtggagc    480
ccgacgacgt ggacgcggcg ccggtgccgg agcggccgag gggcgaggtg gagctgaagc    540
acgtggactt ctcgtacccg tcgcggccgg acatccaggt gttccgcgac ctgagcctcc    600
gtgcgcgcgc cggaagacg ctggcgctgg tgggccgag cgggtgcggc aagagctcgg     660
tgctggctct ggtgcagcgg ttctacaagc ccacgtccgg gcgcgtgttc ttgacggcaa    720
agacgtgcgc aaaaacaacc ttcgggcgtt ccggcgcatt gttgcggtgg tacccaagaa    780
cccgtttcct gttcgcggcg aagaatccac gagaacatcg cgcacgggcg agagggcgct    840 acggaggcg agtggtgga ggcggcggcg caggcgaacg cgcaccggtt catcgcggcg      900
ctgccggaag gggtactgga cgcagaaggg cgagcgcggg gtgcacctgt cgggggcag     960 cggcagcgga tcgcgatcgc gcgcgcgctg gtgaagcagc ggccatcgtg ctgctggacg    1020
aggcgaccag cgcgctggac gccgagtcgg agcggtgcgt gcaggaggcg ctggagcgcg    1080
cggggtccgg gcgcaccacc atcgtggtgg cgcaccggct ggccacggtg cgcggcgcgc    1140
acaccatcgc ggtcatcgac gacggcaagg tggcggagca ggggtcgcac tcgcacctgc    1200
```

-continued

```
tcaagcacca tcccgacggg tgctacgcgc ggatgctgca gctgcagcgg ctgacgggcg   1260
cggcggc                                                              1267

<210> SEQ ID NO 3
<211> LENGTH: 1261
<212> TYPE: DNA
<213> ORGANISM: Sorghum bicolor
<220> FEATURE:
<221> NAME/KEY: CDS
<222> LOCATION: (1)..(1245)

<400> SEQUENCE: 3 ctc ctc gcc gtg ttc ccg ctc gtc gtg ggc gcc acc gtg ctg cag aag     48
Leu Leu Ala Val Phe Pro Leu Val Val Gly Ala Thr Val Leu Gln Lys
 1               5                  10                  15 atg ttc atg aag ggc ttc tcg ggg gac ctg gag gcc gcg cac gcc agg     96
Met Phe Met Lys Gly Phe Ser Gly Asp Leu Glu Ala Ala His Ala Arg
             20                  25                  30 gcc acg cag atc gcg ggc gag gcc gtg gcc aac ctg cgc acc gtg gcc    144
Ala Thr Gln Ile Ala Gly Glu Ala Val Ala Asn Leu Arg Thr Val Ala
         35                  40                  45 gcg ttc aac gcg gag cgc aag atc acg ggg ctg ttc gag gcc aac ctg    192
Ala Phe Asn Ala Glu Arg Lys Ile Thr Gly Leu Phe Glu Ala Asn Leu
     50                  55                  60 cgc ggc ccg ctc cgg cgc tgc ttc tgg aag ggg cag atc gcc ggc agc    240
Arg Gly Pro Leu Arg Arg Cys Phe Trp Lys Gly Gln Ile Ala Gly Ser
 65                  70                  75                  80 ggc tac ggc gtg gcg cag ttc ctg ctg tac gcg tcc tac gcg ctg ggg    288
Gly Tyr Gly Val Ala Gln Phe Leu Leu Tyr Ala Ser Tyr Ala Leu Gly
                 85                  90                  95 ctg tgg tac gcg gcg tgg ctg gtg aag cac ggc gtg tcc gac ttc tcg    336
Leu Trp Tyr Ala Ala Trp Leu Val Lys His Gly Val Ser Asp Phe Ser
            100                 105                 110 cgc acc atc cgc gtg ttc atg gtg ctg atg gtg tcc gcc aac ggc gcc    384
Arg Thr Ile Arg Val Phe Met Val Leu Met Val Ser Ala Asn Gly Ala
        115                 120                 125 gcc gag acg ctg acg ctg gcg ccg gac ttt gtc aag ggc ggg cgc gcg    432
Ala Glu Thr Leu Thr Leu Ala Pro Asp Phe Val Lys Gly Gly Arg Ala
    130                 135                 140 atg cgg tcc gtg ttc gag acc atc gac cgg aaa acg gag gtg gag ccc    480
Met Arg Ser Val Phe Glu Thr Ile Asp Arg Lys Thr Glu Val Glu Pro
145                 150                 155                 160 gac gac gtg gac gcg gcg ccg gtg ccg gag cgg ccc aag ggc gag gtg    528
Asp Asp Val Asp Ala Ala Pro Val Pro Glu Arg Pro Lys Gly Glu Val
                165                 170                 175 gag ctg aag cac gtg gac ttc tcg tac ccg tcg cgg ccg gac atc cag    576
Glu Leu Lys His Val Asp Phe Ser Tyr Pro Ser Arg Pro Asp Ile Gln
            180                 185                 190 gtg ttc cgc gac ctg agc ctc cgg gcg cgc gcc ggg aag acg ctg gcg    624
Val Phe Arg Asp Leu Ser Leu Arg Ala Arg Ala Gly Lys Thr Leu Ala
        195                 200                 205 ctg gtg ggt ccg agc ggg tgc ggc aag agc tcg gtg ctg gcg ctg gtg    672
Leu Val Gly Pro Ser Gly Cys Gly Lys Ser Ser Val Leu Ala Leu Val
    210                 215                 220 cag cgg ttc tac gag ccc acg tcc ggg cgc gtg ctc ctg gac ggc aag    720
Gln Arg Phe Tyr Glu Pro Thr Ser Gly Arg Val Leu Leu Asp Gly Lys
225                 230                 235                 240 gac gtg cgc aag tac aac ctg cgg gcg ctg cgg cgc gtg gtg gcg gtg    768
Asp Val Arg Lys Tyr Asn Leu Arg Ala Leu Arg Arg Val Val Ala Val
                245                 250                 255
```

```
gcg ccg cag gag ccg ttc ctg ttc gcg gcg agc atc cac gac aac atc      816
Ala Pro Gln Glu Pro Phe Leu Phe Ala Ala Ser Ile His Asp Asn Ile
        260                 265                 270 gcg tac ggg cgc gag ggc gcg acg gag gcg gag gtg gtg gag gcg gcg      864
Ala Tyr Gly Arg Glu Gly Ala Thr Glu Ala Glu Val Val Glu Ala Ala
            275                 280                 285 acg cag gcg aac gcg cac cgg ttc atc gcg gcg ctg ccg gag ggc tac      912
Thr Gln Ala Asn Ala His Arg Phe Ile Ala Ala Leu Pro Glu Gly Tyr
        290                 295                 300 ggg acg cag gtg ggc gag cgc ggg gtg cag ctg tcg ggc ggg cag cgg      960
Gly Thr Gln Val Gly Glu Arg Gly Val Gln Leu Ser Gly Gly Gln Arg
305                 310                 315                 320 cag cgg atc gcg atc gcg cgc gct ggt aag cag cgg cca tcg tgc tgc     1008
Gln Arg Ile Ala Ile Ala Arg Ala Gly Lys Gln Arg Pro Ser Cys Cys
                325                 330                 335 tgg acg agg cga cca gcg cgc tgg acg ccg agt cgg agc ggt gcg tgc     1056
Trp Thr Arg Arg Pro Ala Arg Trp Thr Pro Ser Arg Ser Gly Ala Cys
            340                 345                 350 agg agg cgc tgg agc gcg cgg ggt ccg ggc gca cca cca tcg tgg tgg     1104
Arg Arg Arg Trp Ser Ala Arg Gly Pro Gly Ala Pro Pro Ser Trp Trp
        355                 360                 365 cgc acc ggc tgg cca cgg tgc gcg gcg cgc aca cca tcg cgg tca tcg     1152
Arg Thr Gly Trp Pro Arg Cys Ala Ala Arg Thr Pro Ser Arg Ser Ser
370                 375                 380 acg acg gca agg tgg cgg agc agg ggt cgc act cgc acc tgc tca agc     1200
Thr Thr Ala Arg Trp Arg Ser Arg Gly Arg Thr Arg Thr Cys Ser Ser
385                 390                 395                 400 acc atc ccg acg ggt gct acg cgc gga tgc tgc agc tgc agc ggc         1245
Thr Ile Pro Thr Gly Ala Thr Arg Gly Cys Cys Ser Cys Ser Gly
                405                 410                 415 tgacgggcgc ggcggc                                                   1261

<210> SEQ ID NO 4
<211> LENGTH: 415
<212> TYPE: PRT
<213> ORGANISM: Sorghum bicolor

<400> SEQUENCE: 4

Leu Leu Ala Val Phe Pro Leu Val Val Gly Ala Thr Val Leu Gln Lys
  1               5                  10                  15

Met Phe Met Lys Gly Phe Ser Gly Asp Leu Glu Ala Ala His Ala Arg
             20                  25                  30

Ala Thr Gln Ile Ala Gly Glu Ala Val Ala Asn Leu Arg Thr Val Ala
         35                  40                  45

Ala Phe Asn Ala Glu Arg Lys Ile Thr Gly Leu Phe Glu Ala Asn Leu
     50                  55                  60

Arg Gly Pro Leu Arg Arg Cys Phe Trp Lys Gly Gln Ile Ala Gly Ser
 65                  70                  75                  80

Gly Tyr Gly Val Ala Gln Phe Leu Leu Tyr Ala Ser Tyr Ala Leu Gly
                 85                  90                  95

Leu Trp Tyr Ala Ala Trp Leu Val Lys His Gly Val Ser Asp Phe Ser
            100                 105                 110

Arg Thr Ile Arg Val Phe Met Val Leu Met Val Ser Ala Asn Gly Ala
        115                 120                 125

Ala Glu Thr Leu Thr Leu Ala Pro Asp Phe Val Lys Gly Gly Arg Ala
    130                 135                 140

Met Arg Ser Val Phe Glu Thr Ile Asp Arg Lys Thr Glu Val Glu Pro
145                 150                 155                 160
```

Asp Asp Val Asp Ala Ala Pro Val Pro Glu Arg Pro Lys Gly Glu Val
            165                 170                 175
Glu Leu Lys His Val Asp Phe Ser Tyr Pro Ser Arg Pro Asp Ile Gln
            180                 185                 190
Val Phe Arg Asp Leu Ser Leu Arg Ala Arg Ala Gly Lys Thr Leu Ala
            195                 200                 205
Leu Val Gly Pro Ser Gly Cys Gly Lys Ser Ser Val Leu Ala Leu Val
        210                 215                 220
Gln Arg Phe Tyr Glu Pro Thr Ser Gly Arg Val Leu Asp Gly Lys
225                 230                 235                 240
Asp Val Arg Lys Tyr Asn Leu Arg Ala Leu Arg Arg Val Val Ala Val
            245                 250                 255
Ala Pro Gln Glu Pro Phe Leu Phe Ala Ala Ser Ile His Asp Asn Ile
            260                 265                 270
Ala Tyr Gly Arg Glu Gly Ala Thr Glu Ala Glu Val Val Glu Ala Ala
            275                 280                 285
Thr Gln Ala Asn Ala His Arg Phe Ile Ala Ala Leu Pro Glu Gly Tyr
            290                 295                 300
Gly Thr Gln Val Gly Glu Arg Gly Val Gln Leu Ser Gly Gly Gln Arg
305                 310                 315                 320
Gln Arg Ile Ala Ile Ala Arg Ala Gly Lys Gln Arg Pro Ser Cys Cys
            325                 330                 335
Trp Thr Arg Arg Pro Ala Arg Trp Thr Pro Ser Arg Ser Gly Ala Cys
            340                 345                 350
Arg Arg Arg Trp Ser Ala Arg Gly Pro Gly Ala Pro Ser Trp Trp
            355                 360                 365
Arg Thr Gly Trp Pro Arg Cys Ala Ala Arg Thr Pro Ser Arg Ser Ser
        370                 375                 380
Thr Thr Ala Arg Trp Arg Ser Arg Gly Arg Thr Arg Thr Cys Ser Ser
385                 390                 395                 400
Thr Ile Pro Thr Gly Ala Thr Arg Gly Cys Cys Ser Cys Ser Gly
            405                 410                 415

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence:
      oligonucleotide primer designed from sequence of Zea mays Br2
      gene

<400> SEQUENCE: 5
ctcctcgccg tgttcccgct cgtcgt                                        26

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence:
      oligonucleotide primer designed from sequence of Zea mays Br2
      gene

<400> SEQUENCE: 6
gccgccgcgc ccgtcag                                                  17

<210> SEQ ID NO 7

<211> LENGTH: 6827
<212> TYPE: DNA
<213> ORGANISM: Sorghum bicolor

<400> SEQUENCE: 7

| | | | | | |
|---|---|---|---|---|---|
| gtccctcccc | ggcccccgat | cgatgtctac | caacgacccg | gacgagatca | gggcgcgcgt | 60 |
| cgtcgtcctc | ggcgcccctc | atgccgacga | cgacgccggc | gacgagtggg | cccgccccga | 120 |
| gctcgaggcc | ttccacctcc | cctctcccgc | ccaccagcct | cctggcttcc | acctagccgc | 180 |
| tgggcaccaa | ccggaagctg | cagcagagca | acccaccacg | ctccctgctg | cccgccgcac | 240 |
| cagcgacaca | tccactgctg | ctggtgctgc | tcctccttct | ccttcgccgc | ctccgccgcc | 300 |
| ggctcctttg | gagatggacc | agccgcccaa | tgccaagccg | gcctcctcct | ccgccgccgc | 360 |
| cgccggcgcc | aatgacaaca | agaagcccac | cccgcccgcc | gcgctgcgcg | acctcttccg | 420 |
| cttcgccgac | ggcctcgact | gcgcgctcat | gctcgtcggc | acgctcggcg | cgctcgtcca | 480 |
| cggctgctcg | ctccccgtct | tcctccgctt | cttcgccgac | ctcgtcgact | ccttcggctc | 540 |
| ccacgccaac | gacccggaca | ccatggtccg | cctcgtcgtc | aagtacgcct | tctacttcct | 600 |
| cgtcgtcgga | gccgcaatct | gggcgtcctc | atgggcaggt | aaccaacgtt | attcctcctc | 660 |
| ctcctccccct | ccctcctccc | ggcactgctg | ctcgcgtcgc | gaattgtctg | tcgatttgga | 720 |
| ttggatggcg | aatcacatca | gtcgctcaat | cttcatggcc | catggctagc | aatgagatcg | 780 |
| accttcgaat | ccctcgcttg | cagagatctc | ctgctggatg | tggaccggcg | agcggcagtc | 840 |
| gacgcggatg | cggatccggt | acctggacgc | ggcgctgcgc | caggacgtgt | ccttcttcga | 900 |
| caccgacgtg | cgcacctcgg | acgtcatcta | cgccatcaac | gcggacgccg | tggtgggtgc | 960 |
| aggacgccat | cagcgagaag | ctgggcaacc | tcatccacta | catggccacc | ttcgtggcgg | 1020 |
| gcttcgtcgt | gggcttcacc | gccgcctggc | agctggcgct | cgtcacgctc | gccgtcgtgc | 1080 |
| cgctcatcgc | cgtcatcggg | gggctcagcg | ccgccgcgct | cgccaagctc | tcctccagga | 1140 |
| gccaggacgc | gctgtcgggc | gccagcggca | tcgcggagca | ggcgctcgcg | cagatacgga | 1200 |
| tcgtgcaggc | cttcgtcggc | gaggagcgcg | aaatgcgggc | gtactcggcg | cgcttggccg | 1260 |
| tcgcgcagaa | gatcggctac | cgcagcggct | tcgccaaggg | gctcggcctc | ggcggcacct | 1320 |
| acttcaccgt | cttctgctgc | tacggcctcc | tgctctggta | cggcggacac | ctcgtccgcg | 1380 |
| gaaccacacc | aacggagggc | tcgccatcgc | caccatgttc | tccgtcatga | tcggcgggct | 1440 |
| gtaagatgat | cagtttctcc | cgggctctcc | tgttcttccg | tcatgacaca | gcatgtacta | 1500 |
| cgtacgctta | ctggtctgtg | tctgtgtgtg | tgtggatcgc | ctgcgtccag | ggccctcggg | 1560 |
| cagtcggcgc | cgagcatggc | cgcgttcgcc | aaggcgcgcg | tggcggccgc | caagatcttc | 1620 |
| cgcatcatcg | accacaggcc | gggcatctcc | tcgcgggacg | gcgaggacgg | cggcggcgtg | 1680 |
| gagctggagt | cggtgacggg | gcgggtggag | atgaggggcg | tggacttcgc | gtacccgtcg | 1740 |
| cggccggacg | tccccatcct | gcgcggcttc | tcgctcagcg | tgcccgccgg | caagaccatc | 1800 |
| gcgctggtgg | gcagctccgg | ctccgggaag | agcacggtgg | tgtcgctcct | cgagaggttc | 1860 |
| tacgacccca | gcgcaggtat | acatagtacg | ctaccaattc | tagctttagc | gcattgatta | 1920 |
| attagtgttg | gagttcactt | gcttgccaat | tgccattgcc | atcacacatc | agcagctacc | 1980 |
| atacattgcc | aactgccatt | gctgctgcct | tgctgggtgg | ttagtagggg | aagaagcttc | 2040 |
| cactgtagca | ggagtacatt | gcaaacagga | agtgaatttt | gcacgtggga | aatgaagaag | 2100 |
| tgaatgcttg | gagcagagct | ggccggcctc | atgggctgct | tacctactat | ctagtcaacc | 2160 |
| aagcatccct | gtttcttcct | tgtttatggt | caaggcattc | acaccagctt | agaaacttag | 2220 |

```
aaagaagcta agcccttttgt tttaatttttc ctaaaaaaaa attttttggtt aaaatttttt     2280 taaagtttcc cttgtccaca atcccaaatt cttttaagaa gtattaatat atgacgaaaa     2340
ttaaaaccta attgcaccag ttttggtcga aattgaccga aaacgatctt ttgagcctaa     2400
ttagtcccat gattggacaa tatttgtcaa atacaaacga aagtgctgcc gtatcgattt     2460
tgcaaaggtt ttcggaacta aacaaagcct ggtgcctgca acgcgagaca agaaaaacta     2520
tttgcctggc aagatgccac tattgcacat gcatgccact cttttgagcct tgaccgactg     2580 actgactact cagagtagga gtggttcaat tgtattgaca tgtagtagga gtactcgtat     2640
gctatagtag tcctgtagct ttttcaaaca aaaaaaaaag agaaagaaag aaatgaagtc     2700
tgaaatttgt tggttttggc agggcaaatc ttgctggacg ggcatgatct caagtcgctg     2760
aagctccggt ggctccggca gcagattggt ctggtgagcc aggagccgac gctgttcgcg     2820
acgagcatca aggagaacct gctgctgggg cgggacagtc agagtgcgac gcaggccgag     2880
atggaggagg ccgccagggt ggccaacgcg cactccttca tcgtcaagct ccccgacggc     2940
tacgacacgc aggtccgtcc cgtatagcta gctcactagc tgcactgcca cttctctcgc     3000
ttgctcccca ccgttgctgc ctgttgctct ccaatccact tgtcggtgtc tggaccacac     3060
gtgcctgctt gcctagctgc tccacatctg ctttccctgt ccaaccttat gcaactcact     3120
ctaatactat atcaaataca tttctagagt ttaaagctta tcttagaata aatgcatctt     3180
tagctacgag acaacctaac ttcagttgtt gttgttgttt tttttacttt ctctcttctc     3240
acaaatacta tgattacgtc tttacagcga tctttttttat tccaaaccta aaaatgcatg     3300
cactcactct aaaagcgcaa agggagcatc ttttttttccc ccatcatctg cacgcagcct     3360
tttcttttcc tcatgtcacg agggactgaa ggtgtgtatg cagcgtcaag tcatccatcc     3420
gttccacttg gattaggacg gggggccaa ttttttaggcc ccttgttgcc attcgcattt     3480
tgttgttgtg ggtttgccaa caagaaactt gccaggttgc ttttgttatc acgcacagga     3540
caggagaggt cttttttctcg acacaagctc tacagcctct actaaactag cacttgctga     3600
tgagagcaga ggatgaatgg acgatgaaca tctagagtga gagagaaaaa aatgttaata     3660
ataataaaaa gtagtagcag gattaagaat caacctgggg tacgtaggaa gaggtacaat     3720
ccctaggaat ctagagtatg agaagtatgg gaggagttgg gggagtggaa cggaacaaat     3780
tccgagttgg tattttgccg ggaatgtcaa gttgattttt gatcctagtg caagcaagaa     3840
ttatcaatca ctcagactca gcctgtctgt gtctgtccac cccagctctt gctactctac     3900
ttactactgt gctactagtg gtagggtagg tatcttacat aaactgttat tataaactgt     3960
catctgagaa agagagccag tcaaacccat gctgctgctt atttttaatca ctgtcaaatg     4020 gcaggcaggc aggcagtctg gttagttaat aacatctggg aagggtttaa tcaaaccaaa     4080
tcaaatcaga cgaaatctag aggccacatg ggatggggcc atatgtactg tactagcata     4140
actagcggct agatttttatt agaacacgga ctcacactcc cataactata actgacttga     4200
tcatgattcc ttgccaagca atgctcgcat gcccatgcat gcatcatccc tggtcaaact     4260
caaacactct ccaccgtcag ggaataagac ttattatttt attaacaatt caattttttat     4320 ttattaatta cgtctggacg aggagtactg gtttatttga tgagagacat ggcagtccaa     4380
gtcaaactcg tttgtctgac catggcggtg atggccggtg caggttgggg agcgcggcct     4440
gcagctctcc ggtgggcaga agcagcgcat cgccatcgcc cgcgccatgc tcaagaaccc     4500
cgccatcctg ctgctggacg aggccaccag cgcgctggac tccgagtctg agaagctcgt     4560
```

```
gcaggaggcg ctggaccgct tcatgatcgg gcgcaccacc ctggtgatcg cgcacaggat    4620
gtccaccatc cgcaaggccg acgtggtggc cgtgctgcag ggcggccccg tctccgagat    4680
gggcgcgcac gacgagttga tggccaaggg cgagaacggc acttacgcca agttcatccg    4740
catgcaggag caggcgcacg aggcggcgtt cgtcaacgcc cgccgcagca gcgccaggcc    4800
ctccagcgcc cgcaactccg tcagctcgcc catcatgacg cgcaactcct cctacggccg    4860
ctccccatac tcccgccgcc tctccgactt ctccacctcc gacttcaccc tctccatcca    4920
cgacccgcac caccaccacc ggacgatggc cgacaagcag ctcgcgttcc gcgccggcgc    4980
cagctccttc ctccgcctcg ccaggatgaa ctcgcccgag tgggcctacg cgctcgtcgg    5040
ctccctgggc tccatggtct gcggctcctt cagcgccatc ttcgcctaca tcctcagcgc    5100
cgtgctcagc gtctactacg cgccggaccc tcgctacatg aagcgcgaga tcgccaagta    5160
ctgctacctg ctcatcggca tgtcctccgc ggcgctgctg ttcaacacgg tgcagcacgt    5220
gttctgggac acggtcggcg agaacctcac gaagcgtgtg cgcgagaaga tgttcgccgc    5280
cgtgctccgc aacgagatcg cctggttcga cgccgacgag aacgccagcg cgcgcgtcgc    5340
cgccaggctc gcgctcgacg cccagaacgt gcgctccgcc atcggggacc gtatctccgt    5400
catcgtccag aactcggcgc tcatgctcgt cgcctgcacc gcgggcttcg tcctccagtg    5460
gcgcctcgcg ctcgtgctcc tcgccgtctt cccgctcgtc gtgccgcca ccgtgctgca    5520
gaagatgttc atgaagggct ctcggggga cctggaggcc gcgcacgcca gggccacgca    5580
gatcgcgggc gaggccgtgg ccaacctgcg caccgtggcc gcgttcaacg cggagcgcaa    5640
gatcacgggg ctgttcgagg ccaacctgcg cggcccgctc cggcgctgct tctggaaggg    5700
gcagatcgcc ggcagcggct acggcgtggc gcagttcctg ctgtacgcgt cctacgcgct    5760
ggggctgtgg tacgcggcgt ggctggtgaa gcacggcgtg tccgacttct cgcgcaccat    5820
ccgcgtgttc atggtgctga tggtgtccgc caacggcgcc gccgagacgc tgacgctggc    5880
gccggacttt gtcaagggcg ggcgcgcgat gcggtccgtg ttcgagacca tcgaccggaa    5940
aacggaggtg gagcccgacg acgtggacgc ggcgccggtg ccggagcggc caagggcga    6000
ggtggagctg aagcacgtgg acttctcgta cccgtcgcgg ccggacatcc aggtgttccg    6060
cgacctgagc ctccgggcgc gcgccgggaa gacgctggcg ctggtgggtc cgagcgggtg    6120
cggcaagagc tcggtgctgg cgctggtgca gcggttctac gagcccacgt ccgggcgcgt    6180
gctcctggac ggcaaggacg tgcgcaagta caacctgcgg gcgctgcggc gcgtggtggc    6240
ggtggcgccg caggagccgt tcctgttcgc ggcgagcatc cacgacaaca tcgcgtacgg    6300
gcgcgagggc gcgacggagg cggaggtggt ggaggcggcg acgcaggcga acgcgcaccg    6360
gttcatcgcg gcgctgccgg agggctacgg gacgcaggtg ggcgagcgcg gggtgcagct    6420
gtcgggcggg cagcggcagc ggatcgcgat cgcgcgcgcg ctggtgaagc aggcggccat    6480
cgtgctgctg gacgaggcga ccagcgcgct ggacgccgag tcggagcggt gcgtgcagga    6540
ggcgctggag cgcgcgggt ccgggcgcac caccatcgtg gtggcgcacc ggctggccac    6600
ggtgcgcggc gcgcacacca tcgcggtcat cgacgacggc aaggtggcgg agcagggtc    6660
gcactcgcac ctgctcaagc accatcccga cgggtgctac gcgcggatgc tgcagctgca    6720
gcggctgacg ggcgggtgcc gcgcccgggc cgccgccgtc gtcgtccaac ggggccgccg    6780
cgtaggatgg atggatggat catggatgag tttggttcct tgataaa              6827
```

<210> SEQ ID NO 8
<211> LENGTH: 4213

-continued

```
<212> TYPE: DNA
<213> ORGANISM: Sorghum bicolor
<220> FEATURE:
<221> NAME/KEY: CDS
<222> LOCATION: (1)..(4206)

<400> SEQUENCE: 8
```

| | | | | | | | | | | | | | | | | |
|---|---|---|---|---|---|---|---|---|---|---|---|---|---|---|---|---|
| atg | tct | acc | aac | gac | ccg | gac | gag | atc | agg | gcg | cgc | gtc | gtc | gtc | ctc | 48 |
| Met | Ser | Thr | Asn | Asp | Pro | Asp | Glu | Ile | Arg | Ala | Arg | Val | Val | Val | Leu | |
| 1 | | | | 5 | | | | | 10 | | | | | 15 | | |
| ggc | gcc | cct | cat | gcc | gac | gac | gac | gcc | ggc | gac | gag | tgg | gcc | cgc | ccc | 96 |
| Gly | Ala | Pro | His | Ala | Asp | Asp | Asp | Ala | Gly | Asp | Glu | Trp | Ala | Arg | Pro | |
| | | | 20 | | | | | 25 | | | | | 30 | | | |
| gag | ctc | gag | gcc | ttc | cac | ctc | ccc | tct | ccc | gcc | cac | cag | cct | cct | ggc | 144 |
| Glu | Leu | Glu | Ala | Phe | His | Leu | Pro | Ser | Pro | Ala | His | Gln | Pro | Pro | Gly | |
| | | 35 | | | | | 40 | | | | | 45 | | | | |
| ttc | cac | cta | gcc | gct | ggg | cac | caa | ccg | gaa | gct | gca | gca | gag | caa | ccc | 192 |
| Phe | His | Leu | Ala | Ala | Gly | His | Gln | Pro | Glu | Ala | Ala | Ala | Glu | Gln | Pro | |
| | 50 | | | | | 55 | | | | | 60 | | | | | |
| acc | acg | ctc | cct | gct | gcc | cgc | cgc | acc | agc | gac | aca | tcc | act | gct | gct | 240 |
| Thr | Thr | Leu | Pro | Ala | Ala | Arg | Arg | Thr | Ser | Asp | Thr | Ser | Thr | Ala | Ala | |
| 65 | | | | | 70 | | | | | 75 | | | | | 80 | |
| ggt | gct | gct | cct | cct | tct | cct | tcg | ccg | cct | ccg | ccg | ccg | gct | cct | ttg | 288 |
| Gly | Ala | Ala | Pro | Pro | Ser | Pro | Ser | Pro | Pro | Pro | Pro | Pro | Ala | Pro | Leu | |
| | | | | 85 | | | | | 90 | | | | | 95 | | |
| gag | atg | gac | cag | ccg | ccc | aat | gcc | aag | ccg | gcc | tcc | tcc | tcc | gcc | gcc | 336 |
| Glu | Met | Asp | Gln | Pro | Pro | Asn | Ala | Lys | Pro | Ala | Ser | Ser | Ser | Ala | Ala | |
| | | | 100 | | | | | 105 | | | | | 110 | | | |
| gcc | gcc | ggc | gcc | aat | gac | aac | aag | aag | ccc | acc | ccg | ccc | gcc | gcg | ctg | 384 |
| Ala | Ala | Gly | Ala | Asn | Asp | Asn | Lys | Lys | Pro | Thr | Pro | Pro | Ala | Ala | Leu | |
| | | 115 | | | | | 120 | | | | | 125 | | | | |
| cgc | gac | ctc | ttc | cgc | ttc | gcc | gac | ggc | ctc | gac | tgc | gcg | ctc | atg | ctc | 432 |
| Arg | Asp | Leu | Phe | Arg | Phe | Ala | Asp | Gly | Leu | Asp | Cys | Ala | Leu | Met | Leu | |
| | 130 | | | | | 135 | | | | | 140 | | | | | |
| gtc | ggc | acg | ctc | ggc | gcg | ctc | gtc | cac | ggc | tgc | tcg | ctc | ccc | gtc | ttc | 480 |
| Val | Gly | Thr | Leu | Gly | Ala | Leu | Val | His | Gly | Cys | Ser | Leu | Pro | Val | Phe | |
| 145 | | | | | 150 | | | | | 155 | | | | | 160 | |
| ctc | cgc | ttc | ttc | gcc | gac | ctc | gtc | gac | tcc | ttc | ggc | tcc | cac | gcc | aac | 528 |
| Leu | Arg | Phe | Phe | Ala | Asp | Leu | Val | Asp | Ser | Phe | Gly | Ser | His | Ala | Asn | |
| | | | | 165 | | | | | 170 | | | | | 175 | | |
| gac | ccg | gac | acc | atg | gtc | cgc | ctc | gtc | gtc | aag | tac | gcc | ttc | tac | ttc | 576 |
| Asp | Pro | Asp | Thr | Met | Val | Arg | Leu | Val | Val | Lys | Tyr | Ala | Phe | Tyr | Phe | |
| | | | 180 | | | | | 185 | | | | | 190 | | | |
| ctc | gtc | gtc | gga | gcc | gca | atc | tgg | gcg | tcc | tca | tgg | gca | gag | atc | tcc | 624 |
| Leu | Val | Val | Gly | Ala | Ala | Ile | Trp | Ala | Ser | Ser | Trp | Ala | Glu | Ile | Ser | |
| | | 195 | | | | | 200 | | | | | 205 | | | | |
| tgc | tgg | atg | tgg | acc | ggc | gag | cgg | cag | tcg | acg | cgg | atg | cgg | atc | cgg | 672 |
| Cys | Trp | Met | Trp | Thr | Gly | Glu | Arg | Gln | Ser | Thr | Arg | Met | Arg | Ile | Arg | |
| | 210 | | | | | 215 | | | | | 220 | | | | | |
| tac | ctg | gac | gcg | gcg | ctg | cgg | cag | gac | gtg | tcc | ttc | ttc | gac | acc | gac | 720 |
| Tyr | Leu | Asp | Ala | Ala | Leu | Arg | Gln | Asp | Val | Ser | Phe | Phe | Asp | Thr | Asp | |
| 225 | | | | | 230 | | | | | 235 | | | | | 240 | |
| gtg | cgc | acc | tcg | gac | gtc | atc | tac | gcc | atc | aac | gcg | gac | gcc | gtg | gtg | 768 |
| Val | Arg | Thr | Ser | Asp | Val | Ile | Tyr | Ala | Ile | Asn | Ala | Asp | Ala | Val | Val | |
| | | | | 245 | | | | | 250 | | | | | 255 | | |
| ggt | gca | gga | cgc | cat | cag | cga | gaa | gct | ggg | caa | cct | cat | cca | cta | cat | 816 |
| Gly | Ala | Gly | Arg | His | Gln | Arg | Glu | Ala | Gly | Gln | Pro | His | Pro | Leu | His | |
| | | | 260 | | | | | 265 | | | | | 270 | | | |
| ggc | cac | ctt | cgt | ggc | ggg | ctt | cgt | cgt | ggg | ctt | cac | cgc | cgc | ctg | gca | 864 |
| Gly | His | Leu | Arg | Gly | Gly | Leu | Arg | Arg | Gly | Leu | His | Arg | Arg | Leu | Ala | |
| | 275 | | | | | 280 | | | | | 285 | | | | | |

```
                                                                -continued gct ggc gct cgt cac gct cgc cgt cgt gcc gct cat cgc cgt cat cgg    912
Ala Gly Ala Arg His Ala Arg Arg Arg Ala Ala His Arg Arg His Arg
        290                 295                 300 ggg gct cag cgc cgc cgc gct cgc caa gct ctc ctc cag gag cca gga    960
Gly Ala Gln Arg Arg Arg Ala Arg Gln Ala Leu Leu Gln Glu Pro Gly
305                 310                 315                 320 cgc gct gtc ggg cgc cag cgg cat cgc gga gca ggc gct cgc gca gat   1008
Arg Ala Val Gly Arg Gln Arg His Arg Gly Ala Gly Ala Arg Ala Asp
                325                 330                 335 acg gat cgt gca ggc ctt cgt cgg cga gga gcg cga aat gcg ggc gta   1056
Thr Asp Arg Ala Gly Leu Arg Arg Arg Gly Ala Arg Asn Ala Gly Val
            340                 345                 350 ctc ggc ggc gtt ggc cgt cgc gca gaa gat cgg cta ccg cag cgg ctt   1104
Leu Gly Gly Val Gly Arg Arg Ala Glu Asp Arg Leu Pro Gln Arg Leu
        355                 360                 365 cgc caa ggg gct cgg cct cgg cgg cac cta ctt cac cgt ctt ctg ctg   1152
Arg Gln Gly Ala Arg Pro Arg Arg His Leu Leu His Arg Leu Leu Leu
    370                 375                 380 cta cgg cct cct gct ctg gta cgg cgg aca cct cgt ccg cgg aac cac   1200
Leu Arg Pro Pro Ala Leu Val Arg Arg Thr Pro Arg Pro Arg Asn His
385                 390                 395                 400 acc aac gga ggg ctc gcc atc gcc acc atg ttc tcc gtc atg atc ggc   1248
Thr Asn Gly Gly Leu Ala Ile Ala Thr Met Phe Ser Val Met Ile Gly
                405                 410                 415 ggg ctg gcc ctc ggg cag tcg gcg ccg agc atg gcc gcg ttc gcc aag   1296
Gly Leu Ala Leu Gly Gln Ser Ala Pro Ser Met Ala Ala Phe Ala Lys
            420                 425                 430 gcg cgc gtg gcg gcc gcc aag atc ttc cgc atc atc gac cac agg ccg   1344
Ala Arg Val Ala Ala Ala Lys Ile Phe Arg Ile Ile Asp His Arg Pro
        435                 440                 445 ggc atc tcc tcg cgg gac ggc gag gac ggc ggc gtg gag ctg gag        1392
Gly Ile Ser Ser Arg Asp Gly Glu Asp Gly Gly Val Glu Leu Glu
    450                 455                 460 tcg gtg acg ggg cgg gtg gag atg agg ggc gtg gac ttc gcg tac ccg   1440
Ser Val Thr Gly Arg Val Glu Met Arg Gly Val Asp Phe Ala Tyr Pro
465                 470                 475                 480 tcg cgg ccg gac gtc ccc atc ctg cgc ggc ttc tcg ctc agc gtg ccc   1488
Ser Arg Pro Asp Val Pro Ile Leu Arg Gly Phe Ser Leu Ser Val Pro
                485                 490                 495 gcc ggc aag acc atc gcg ctg gtg ggc agc tcc ggc tcc ggg aag agc   1536
Ala Gly Lys Thr Ile Ala Leu Val Gly Ser Ser Gly Ser Gly Lys Ser
            500                 505                 510 acg gtg gtg tcg ctc ctc gag agg ttc tac gac ccc agc gca ggg caa   1584
Thr Val Val Ser Leu Leu Glu Arg Phe Tyr Asp Pro Ser Ala Gly Gln
        515                 520                 525 atc ttg ctg gac ggg cat gat ctc aag tcg ctg aag ctc cgg tgg ctc   1632
Ile Leu Leu Asp Gly His Asp Leu Lys Ser Leu Lys Leu Arg Trp Leu
    530                 535                 540 cgg cag cag att ggt ctg gtg agc cag gag ccg acg ctg ttc gcg acg   1680
Arg Gln Gln Ile Gly Leu Val Ser Gln Glu Pro Thr Leu Phe Ala Thr
545                 550                 555                 560 agc atc aag gag aac ctg ctg ctg ggg cgg gac agt cag agt gcg acg   1728
Ser Ile Lys Glu Asn Leu Leu Leu Gly Arg Asp Ser Gln Ser Ala Thr
                565                 570                 575 cag gcc gag atg gag gag gcc gcc agg gtg gcc aac gcg cac tcc ttc   1776
Gln Ala Glu Met Glu Glu Ala Ala Arg Val Ala Asn Ala His Ser Phe
            580                 585                 590 atc gtc aag ctc ccc gac ggc tac gac acg cag gtt ggg gag cgc ggc   1824
Ile Val Lys Leu Pro Asp Gly Tyr Asp Thr Gln Val Gly Glu Arg Gly
```

-continued

|     | 595 |     |     |     | 600 |     |     |     | 605 |     |     |     |     |     |      |
|-----|-----|-----|-----|-----|-----|-----|-----|-----|-----|-----|-----|-----|-----|-----|------|
| ctg | cag | ctc | tcc | ggt | ggg | cag | aag | cag | cgc | atc | gcc | atc | gcc | cgc | gcc  | 1872 |
| Leu | Gln | Leu | Ser | Gly | Gly | Gln | Lys | Gln | Arg | Ile | Ala | Ile | Ala | Arg | Ala  |
|     | 610 |     |     |     |     | 615 |     |     |     |     | 620 |     |     |     |      | atg ctc aag aac ccc gcc atc ctg ctg ctg gac gag gcc acc agc gcg    1920
Met Leu Lys Asn Pro Ala Ile Leu Leu Leu Asp Glu Ala Thr Ser Ala
625                 630                 635                 640 ctg gac tcc gag tct gag aag ctc gtg cag gag gcg ctg gac cgc ttc    1968
Leu Asp Ser Glu Ser Glu Lys Leu Val Gln Glu Ala Leu Asp Arg Phe
            645                 650                 655 atg atc ggg cgc acc acc ctg gtg atc gcg cac agg atg tcc acc atc    2016
Met Ile Gly Arg Thr Thr Leu Val Ile Ala His Arg Met Ser Thr Ile
        660                 665                 670 cgc aag gcc gac gtg gtg gcc gtg ctg cag ggc ggc ccc gtc tcc gag    2064
Arg Lys Ala Asp Val Val Ala Val Leu Gln Gly Gly Pro Val Ser Glu
    675                 680                 685 atg ggc gcg cac gac gag ttg atg gcc aag ggc gag aac ggc act tac    2112
Met Gly Ala His Asp Glu Leu Met Ala Lys Gly Glu Asn Gly Thr Tyr
690                 695                 700 gcc aag ttc atc cgc atg cag gag cag gcg cac gag gcg gcg ttc gtc    2160
Ala Lys Phe Ile Arg Met Gln Glu Gln Ala His Glu Ala Ala Phe Val
705             710                 715                 720 aac gcc cgc cgc agc agc gcc agg ccc tcc agc gcc cgc aac tcc gtc    2208
Asn Ala Arg Arg Ser Ser Ala Arg Pro Ser Ser Ala Arg Asn Ser Val
                725                 730                 735 agc tcg ccc atc atg acg cgc aac tcc tcc tac ggc cgc tcc cca tac    2256
Ser Ser Pro Ile Met Thr Arg Asn Ser Ser Tyr Gly Arg Ser Pro Tyr
            740                 745                 750 tcc cgc cgc ctc tcc gac ttc tcc acc tcc gac ttc acc ctc tcc atc    2304
Ser Arg Arg Leu Ser Asp Phe Ser Thr Ser Asp Phe Thr Leu Ser Ile
        755                 760                 765 cac gac ccg cac cac cac cac cgg acg atg gcc gac aag cag ctc gcg    2352
His Asp Pro His His His His Arg Thr Met Ala Asp Lys Gln Leu Ala
    770                 775                 780 ttc cgc gcc ggc gcc agc tcc ttc ctc cgc ctc gcc agg atg aac tcg    2400
Phe Arg Ala Gly Ala Ser Ser Phe Leu Arg Leu Ala Arg Met Asn Ser
785                 790                 795                 800 ccc gag tgg gcc tac gcg ctc gtc ggc tcc ctg ggc tcc atg gtc tgc    2448
Pro Glu Trp Ala Tyr Ala Leu Val Gly Ser Leu Gly Ser Met Val Cys
                805                 810                 815 ggc tcc ttc agc gcc atc ttc gcc tac atc ctc agc gcc gtg ctc agc    2496
Gly Ser Phe Ser Ala Ile Phe Ala Tyr Ile Leu Ser Ala Val Leu Ser
            820                 825                 830 gtc tac tac gcg ccg gac cct cgc tac atg aag cgc gag atc gcc aag    2544
Val Tyr Tyr Ala Pro Asp Pro Arg Tyr Met Lys Arg Glu Ile Ala Lys
        835                 840                 845 tac tgc tac ctc ctc atc ggc atg tcc tcc gcg gcg ctg ctg ttc aac    2592
Tyr Cys Tyr Leu Leu Ile Gly Met Ser Ser Ala Ala Leu Leu Phe Asn
    850                 855                 860 acg gtg cag cac gtg ttc tgg gac acg gtc ggc gag aac ctc acg aag    2640
Thr Val Gln His Val Phe Trp Asp Thr Val Gly Glu Asn Leu Thr Lys
865                 870                 875                 880 cgt gtg cgc gag aag atg ttc gcc gcc gtg ctc cgc aac gag atc gcc    2688
Arg Val Arg Glu Lys Met Phe Ala Ala Val Leu Arg Asn Glu Ile Ala
                885                 890                 895 tgg ttc gac gcc gac gag aac gcc agc gcg cgc gtc gcc gcc agg ctc    2736
Trp Phe Asp Ala Asp Glu Asn Ala Ser Ala Arg Val Ala Ala Arg Leu
            900                 905                 910 gcg ctc gac gcc cag aac gtg cgc tcc gcc atc ggg gac cgt atc tcc    2784

```
Ala Leu Asp Ala Gln Asn Val Arg Ser Ala Ile Gly Asp Arg Ile Ser
    915                 920                 925 gtc atc gtc cag aac tcg gcg ctc atg ctc gtc gcc tgc acc gcg ggc      2832
Val Ile Val Gln Asn Ser Ala Leu Met Leu Val Ala Cys Thr Ala Gly
930                 935                 940 ttc gtc ctc cag tgg cgc ctc gcg ctc gtg ctc ctc gcc gtc ttc ccg      2880
Phe Val Leu Gln Trp Arg Leu Ala Leu Val Leu Leu Ala Val Phe Pro
945                 950                 955                 960 ctc gtc gtg gcc gcc acc gtg ctg cag aag atg ttc atg aag ggc ttc      2928
Leu Val Val Ala Ala Thr Val Leu Gln Lys Met Phe Met Lys Gly Phe
                965                 970                 975 tcg ggg gac ctg gag gcc gcg cac gcc agg gcc acg cag atc gcg ggc      2976
Ser Gly Asp Leu Glu Ala Ala His Ala Arg Ala Thr Gln Ile Ala Gly
            980                 985                 990 gag gcc gtg gcc aac ctg cgc acc gtg gcc gcg ttc aac gcg gag cgc      3024
Glu Ala Val Ala Asn Leu Arg Thr Val Ala Ala Phe Asn Ala Glu Arg
        995                 1000                1005 aag atc acg ggg ctg ttc gag gcc aac ctg cgc ggc ccg ctc cgg cgc      3072
Lys Ile Thr Gly Leu Phe Glu Ala Asn Leu Arg Gly Pro Leu Arg Arg
    1010                1015                1020 tgc ttc tgg aag ggg cag atc gcc ggc agc ggc tac ggc gtg gcg cag      3120
Cys Phe Trp Lys Gly Gln Ile Ala Gly Ser Gly Tyr Gly Val Ala Gln
1025                1030                1035                1040 ttc ctg ctg tac gcg tcc tac gcg ctg ggg ctg tgg tac gcg gcg tgg      3168
Phe Leu Leu Tyr Ala Ser Tyr Ala Leu Gly Leu Trp Tyr Ala Ala Trp
                1045                1050                1055 ctg gtg aag cac ggc gtg tcc gac ttc tcg cgc acc atc cgc gtg ttc      3216
Leu Val Lys His Gly Val Ser Asp Phe Ser Arg Thr Ile Arg Val Phe
            1060                1065                1070 atg gtg ctg atg gtg tcc gcc aac ggc gcc gcc gag acg ctg acg ctg      3264
Met Val Leu Met Val Ser Ala Asn Gly Ala Ala Glu Thr Leu Thr Leu
        1075                1080                1085 gcg ccg gac ttt gtc aag ggc ggg cgc gcg atg cgg tcc gtg ttc gag      3312
Ala Pro Asp Phe Val Lys Gly Gly Arg Ala Met Arg Ser Val Phe Glu
    1090                1095                1100 acc atc gac cgg aaa acg gag gtg gag ccc gac gac gtg gac gcg gcg      3360
Thr Ile Asp Arg Lys Thr Glu Val Glu Pro Asp Asp Val Asp Ala Ala
1105                1110                1115                1120 ccg gtg ccg gag cgg ccc aag ggc gag gtg gag ctg aag cac gtg gac      3408
Pro Val Pro Glu Arg Pro Lys Gly Glu Val Glu Leu Lys His Val Asp
                1125                1130                1135 ttc tcg tac ccg tcg cgg ccg gac atc cag gtg ttc cgc gac ctg agc      3456
Phe Ser Tyr Pro Ser Arg Pro Asp Ile Gln Val Phe Arg Asp Leu Ser
            1140                1145                1150 ctc cgg gcg cgc gcc ggg aag acg ctg gcg ctg gtg ggt ccg agc ggg      3504
Leu Arg Ala Arg Ala Gly Lys Thr Leu Ala Leu Val Gly Pro Ser Gly
        1155                1160                1165 tgc ggc aag agc tcg gtg ctg gcg ctg gtg cag cgg ttc tac gag ccc      3552
Cys Gly Lys Ser Ser Val Leu Ala Leu Val Gln Arg Phe Tyr Glu Pro
    1170                1175                1180 acg tcc ggg cgc gtg ctc ctg gac ggc aag gac gtg cgc aag tac aac      3600
Thr Ser Gly Arg Val Leu Leu Asp Gly Lys Asp Val Arg Lys Tyr Asn
1185                1190                1195                1200 ctg cgg gcg ctg cgg cgc gtg gtg gcg gtg gcg ccg cag gag ccg ttc      3648
Leu Arg Ala Leu Arg Arg Val Val Ala Val Ala Pro Gln Glu Pro Phe
                1205                1210                1215 ctg ttc gcg gcg agc atc cac gac aac atc gcg tac ggg cgc gag ggc      3696
Leu Phe Ala Ala Ser Ile His Asp Asn Ile Ala Tyr Gly Arg Glu Gly
            1220                1225                1230
```

-continued

| | |
|---|---|
| gcg acg gag gcg gag gtg gtg gag gcg gcg acg cag gcg aac gcg cac<br>Ala Thr Glu Ala Glu Val Val Glu Ala Ala Thr Gln Ala Asn Ala His<br>      1235                    1240                   1245 | 3744 |
| cgg ttc atc gcg gcg ctg ccg gag ggc tac ggg acg cag gtg ggc gag<br>Arg Phe Ile Ala Ala Leu Pro Glu Gly Tyr Gly Thr Gln Val Gly Glu<br>      1250                    1255                   1260 | 3792 |
| cgc ggg gtg cag ctg tcg ggc ggg cag cgg cag cgg atc gcg atc gcg<br>Arg Gly Val Gln Leu Ser Gly Gly Gln Arg Gln Arg Ile Ala Ile Ala<br>1265                    1270                    1275                   1280 | 3840 |
| cgc gcg ctg gtg aag cag gcg gcc atc gtg ctg ctg gac gag gcg acc<br>Arg Ala Leu Val Lys Gln Ala Ala Ile Val Leu Leu Asp Glu Ala Thr<br>                    1285                    1290                    1295 | 3888 |
| agc gcg ctg gac gcc gag tcg gag cgg tgc gtg cag gag gcg ctg gag<br>Ser Ala Leu Asp Ala Glu Ser Glu Arg Cys Val Gln Glu Ala Leu Glu<br>1300                    1305                    1310 | 3936 |
| cgc gcg ggg tcc ggg cgc acc acc atc gtg gtg gcg cac cgg ctg gcc<br>Arg Ala Gly Ser Gly Arg Thr Thr Ile Val Val Ala His Arg Leu Ala<br>      1315                    1320                   1325 | 3984 |
| acg gtg cgc ggc gcg cac acc atc gcg gtc atc gac gac ggc aag gtg<br>Thr Val Arg Gly Ala His Thr Ile Ala Val Ile Asp Asp Gly Lys Val<br>                    1330                    1335                    1340 | 4032 |
| gcg gag cag ggg tcg cac tcg cac ctg ctc aag cac cat ccc gac ggg<br>Ala Glu Gln Gly Ser His Ser His Leu Leu Lys His His Pro Asp Gly<br>1345                    1350                    1355                    1360 | 4080 |
| tgc tac gcg cgg atg ctg cag ctg cag cgg ctg acg ggc ggg tgc cgc<br>Cys Tyr Ala Arg Met Leu Gln Leu Gln Arg Leu Thr Gly Gly Cys Arg<br>      1365                    1370                    1375 | 4128 |
| gcc cgg gcc gcc gcc gtc gtc gtc caa cgg ggc cgc cgc gta gga tgg<br>Ala Arg Ala Ala Ala Val Val Val Gln Arg Gly Arg Arg Val Gly Trp<br>                    1380                    1385                    1390 | 4176 |
| atg gat gga tca tgg atg agt ttg gtt cct tgataaa<br>Met Asp Gly Ser Trp Met Ser Leu Val Pro<br>1395                    1400 | 4213 |

<210> SEQ ID NO 9
<211> LENGTH: 1402
<212> TYPE: PRT
<213> ORGANISM: Sorghum bicolor

<400> SEQUENCE: 9

Met Ser Thr Asn Asp Pro Asp Glu Ile Arg Ala Arg Val Val Val Leu
1                 5                    10                  15

Gly Ala Pro His Ala Asp Asp Ala Gly Asp Glu Trp Ala Arg Pro
                 20                    25                  30

Glu Leu Glu Ala Phe His Leu Pro Ser Pro Ala His Gln Pro Pro Gly
               35                    40                    45

Phe His Leu Ala Ala Gly His Gln Pro Glu Ala Ala Ala Glu Gln Pro
    50                    55                    60

Thr Thr Leu Pro Ala Ala Arg Arg Thr Ser Asp Thr Ser Thr Ala Ala
65                 70                    75                    80

Gly Ala Ala Pro Pro Ser Pro Ser Pro Pro Pro Pro Ala Pro Leu
                 85                    90                    95

Glu Met Asp Gln Pro Pro Asn Ala Lys Pro Ala Ser Ser Ser Ala Ala
                100                 105                 110

Ala Ala Gly Ala Asn Asp Asn Lys Lys Pro Thr Pro Pro Ala Ala Leu
        115                    120                 125

Arg Asp Leu Phe Arg Phe Ala Asp Gly Leu Asp Cys Ala Leu Met Leu
    130                    135                    140

-continued

```
Val Gly Thr Leu Gly Ala Leu Val His Gly Cys Ser Leu Pro Val Phe
145                 150                 155                 160

Leu Arg Phe Phe Ala Asp Leu Val Asp Ser Phe Gly Ser His Ala Asn
                165                 170                 175

Asp Pro Asp Thr Met Val Arg Leu Val Val Lys Tyr Ala Phe Tyr Phe
            180                 185                 190

Leu Val Val Gly Ala Ala Ile Trp Ala Ser Ser Trp Ala Glu Ile Ser
        195                 200                 205

Cys Trp Met Trp Thr Gly Glu Arg Gln Ser Thr Arg Met Arg Ile Arg
    210                 215                 220

Tyr Leu Asp Ala Ala Leu Arg Gln Asp Val Ser Phe Phe Asp Thr Asp
225                 230                 235                 240

Val Arg Thr Ser Asp Val Ile Tyr Ala Ile Asn Ala Asp Ala Val Val
                245                 250                 255

Gly Ala Gly Arg His Gln Arg Glu Ala Gly Gln Pro His Pro Leu His
                260                 265                 270

Gly His Leu Arg Gly Gly Leu Arg Arg Gly Leu His Arg Arg Leu Ala
            275                 280                 285

Ala Gly Ala Arg His Ala Arg Arg Ala Ala His Arg Arg His Arg
290                 295                 300

Gly Ala Gln Arg Arg Ala Arg Gln Ala Leu Leu Gln Glu Pro Gly
305                 310                 315                 320

Arg Ala Val Gly Arg Gln Arg His Arg Gly Ala Gly Ala Arg Ala Asp
                325                 330                 335

Thr Asp Arg Ala Gly Leu Arg Arg Gly Ala Arg Asn Ala Gly Val
            340                 345                 350

Leu Gly Gly Val Gly Arg Arg Ala Glu Asp Arg Leu Pro Gln Arg Leu
            355                 360                 365

Arg Gln Gly Ala Arg Pro Arg Arg His Leu Leu His Arg Leu Leu Leu
370                 375                 380

Leu Arg Pro Pro Ala Leu Val Arg Arg Thr Pro Arg Pro Arg Asn His
385                 390                 395                 400

Thr Asn Gly Gly Leu Ala Ile Ala Thr Met Phe Ser Val Met Ile Gly
            405                 410                 415

Gly Leu Ala Leu Gly Gln Ser Ala Pro Ser Met Ala Ala Phe Ala Lys
            420                 425                 430

Ala Arg Val Ala Ala Ala Lys Ile Phe Arg Ile Ile Asp His Arg Pro
            435                 440                 445

Gly Ile Ser Ser Arg Asp Gly Glu Asp Gly Gly Val Glu Leu Glu
450                 455                 460

Ser Val Thr Gly Arg Val Glu Met Arg Gly Val Asp Phe Ala Tyr Pro
465                 470                 475                 480

Ser Arg Pro Asp Val Pro Ile Leu Arg Gly Phe Ser Leu Ser Val Pro
                485                 490                 495

Ala Gly Lys Thr Ile Ala Leu Val Gly Ser Ser Gly Ser Gly Lys Ser
            500                 505                 510

Thr Val Val Ser Leu Leu Glu Arg Phe Tyr Asp Pro Ser Ala Gly Gln
            515                 520                 525

Ile Leu Leu Asp Gly His Asp Leu Lys Ser Leu Lys Leu Arg Trp Leu
530                 535                 540

Arg Gln Gln Ile Gly Leu Val Ser Gln Glu Pro Thr Leu Phe Ala Thr
545                 550                 555                 560

Ser Ile Lys Glu Asn Leu Leu Leu Gly Arg Asp Ser Gln Ser Ala Thr
```

```
                        565                 570                 575
Gln Ala Glu Met Glu Ala Ala Arg Val Ala Asn Ala His Ser Phe
            580                 585                 590

Ile Val Lys Leu Pro Asp Gly Tyr Asp Thr Gln Val Gly Glu Arg Gly
        595                 600                 605

Leu Gln Leu Ser Gly Gly Gln Lys Gln Arg Ile Ala Ile Ala Arg Ala
    610                 615                 620

Met Leu Lys Asn Pro Ala Ile Leu Leu Asp Glu Ala Thr Ser Ala
625                 630                 635                 640

Leu Asp Ser Glu Ser Glu Lys Leu Val Gln Glu Ala Leu Asp Arg Phe
                645                 650                 655

Met Ile Gly Arg Thr Thr Leu Val Ile Ala His Arg Met Ser Thr Ile
            660                 665                 670

Arg Lys Ala Asp Val Val Ala Val Leu Gln Gly Gly Pro Val Ser Glu
        675                 680                 685

Met Gly Ala His Asp Glu Leu Met Ala Lys Gly Glu Asn Gly Thr Tyr
    690                 695                 700

Ala Lys Phe Ile Arg Met Gln Glu Gln Ala His Glu Ala Ala Phe Val
705                 710                 715                 720

Asn Ala Arg Arg Ser Ser Ala Arg Pro Ser Ser Ala Arg Asn Ser Val
                725                 730                 735

Ser Ser Pro Ile Met Thr Arg Asn Ser Ser Tyr Gly Arg Ser Pro Tyr
            740                 745                 750

Ser Arg Arg Leu Ser Asp Phe Ser Thr Ser Asp Phe Thr Leu Ser Ile
        755                 760                 765

His Asp Pro His His His Arg Thr Met Ala Asp Lys Gln Leu Ala
    770                 775                 780

Phe Arg Ala Gly Ala Ser Ser Phe Leu Arg Leu Ala Arg Met Asn Ser
785                 790                 795                 800

Pro Glu Trp Ala Tyr Ala Leu Val Gly Ser Leu Gly Ser Met Val Cys
                805                 810                 815

Gly Ser Phe Ser Ala Ile Phe Ala Tyr Ile Leu Ser Ala Val Leu Ser
            820                 825                 830

Val Tyr Tyr Ala Pro Asp Pro Arg Tyr Met Lys Arg Glu Ile Ala Lys
        835                 840                 845

Tyr Cys Tyr Leu Leu Ile Gly Met Ser Ser Ala Ala Leu Leu Phe Asn
850                 855                 860

Thr Val Gln His Val Phe Trp Asp Thr Val Gly Glu Asn Leu Thr Lys
865                 870                 875                 880

Arg Val Arg Glu Lys Met Phe Ala Ala Val Leu Arg Asn Glu Ile Ala
                885                 890                 895

Trp Phe Asp Ala Asp Glu Asn Ala Ser Ala Arg Val Ala Ala Arg Leu
            900                 905                 910

Ala Leu Asp Ala Gln Asn Val Arg Ser Ala Ile Gly Asp Arg Ile Ser
        915                 920                 925

Val Ile Val Gln Asn Ser Ala Leu Met Leu Val Ala Cys Thr Ala Gly
    930                 935                 940

Phe Val Leu Gln Trp Arg Leu Ala Leu Val Leu Leu Ala Val Phe Pro
945                 950                 955                 960

Leu Val Val Ala Ala Thr Val Leu Gln Lys Met Phe Met Lys Gly Phe
                965                 970                 975

Ser Gly Asp Leu Glu Ala Ala His Ala Arg Ala Thr Gln Ile Ala Gly
            980                 985                 990
```

```
Glu Ala Val Ala Asn Leu Arg Thr Val Ala Ala Phe Asn Ala Glu Arg
        995                 1000                1005
Lys Ile Thr Gly Leu Phe Glu Ala Asn Leu Arg Gly Pro Leu Arg Arg
    1010                1015                1020
Cys Phe Trp Lys Gly Gln Ile Ala Gly Ser Gly Tyr Gly Val Ala Gln
1025                1030                1035                1040
Phe Leu Leu Tyr Ala Ser Tyr Ala Leu Gly Leu Trp Tyr Ala Ala Trp
            1045                1050                1055
Leu Val Lys His Gly Val Ser Asp Phe Ser Arg Thr Ile Arg Val Phe
        1060                1065                1070
Met Val Leu Met Val Ser Ala Asn Gly Ala Ala Glu Thr Leu Thr Leu
        1075                1080                1085
Ala Pro Asp Phe Val Lys Gly Gly Arg Ala Met Arg Ser Val Phe Glu
        1090                1095                1100
Thr Ile Asp Arg Lys Thr Glu Val Glu Pro Asp Val Asp Ala Ala
1105                1110                1115                1120
Pro Val Pro Glu Arg Pro Lys Gly Glu Val Glu Leu Lys His Val Asp
            1125                1130                1135
Phe Ser Tyr Pro Ser Arg Pro Asp Ile Gln Val Phe Arg Asp Leu Ser
            1140                1145                1150
Leu Arg Ala Arg Ala Gly Lys Thr Leu Ala Leu Val Gly Pro Ser Gly
        1155                1160                1165
Cys Gly Lys Ser Ser Val Leu Ala Leu Val Gln Arg Phe Tyr Glu Pro
    1170                1175                1180
Thr Ser Gly Arg Val Leu Leu Asp Gly Lys Asp Val Arg Lys Tyr Asn
1185                1190                1195                1200
Leu Arg Ala Leu Arg Arg Val Val Ala Val Ala Pro Gln Glu Pro Phe
            1205                1210                1215
Leu Phe Ala Ala Ser Ile His Asp Asn Ile Ala Tyr Gly Arg Glu Gly
            1220                1225                1230
Ala Thr Glu Ala Glu Val Val Glu Ala Ala Thr Gln Ala Asn Ala His
        1235                1240                1245
Arg Phe Ile Ala Ala Leu Pro Glu Gly Tyr Gly Thr Gln Val Gly Glu
        1250                1255                1260
Arg Gly Val Gln Leu Ser Gly Gly Gln Arg Gln Arg Ile Ala Ile Ala
1265                1270                1275                1280
Arg Ala Leu Val Lys Gln Ala Ala Ile Val Leu Leu Asp Glu Ala Thr
            1285                1290                1295
Ser Ala Leu Asp Ala Glu Ser Glu Arg Cys Val Gln Glu Ala Leu Glu
            1300                1305                1310
Arg Ala Gly Ser Gly Arg Thr Thr Ile Val Val Ala His Arg Leu Ala
        1315                1320                1325
Thr Val Arg Gly Ala His Thr Ile Ala Val Ile Asp Asp Gly Lys Val
        1330                1335                1340
Ala Glu Gln Gly Ser His Ser His Leu Leu Lys His His Pro Asp Gly
1345                1350                1355                1360
Cys Tyr Ala Arg Met Leu Gln Leu Gln Arg Leu Thr Gly Gly Cys Arg
            1365                1370                1375
Ala Arg Ala Ala Ala Val Val Val Gln Arg Gly Arg Arg Val Gly Trp
            1380                1385                1390
Met Asp Gly Ser Trp Met Ser Leu Val Pro
        1395                1400
```

US 6,750,380 B1

ISOLATED NUCLEIC ACID MOELCULES ENCODING THE DW3 P-GLYCOPROTEIN OF SORGHUM AND METHODS OF MODIFYING GROWTH IN TRANSGENIC PLANTS THEREWITH

CROSS-REFERENCE TO RELATED APPLICATIONS

This application claims the benefit of U.S. Provisional Application No. 60/165,176, filed Nov. 12, 1999.

FIELD OF THE INVENTION

The present invention relates to the genetic manipulation of organisms, particularly plants, with genes that control growth and development. The invention further relates to genes that control growth, including homologues and mutant forms, the proteins encoded therefrom and plants transformed with these genes.

BACKGROUND OF THE INVENTION

Dwarf plants have had a major impact on agriculture. Dwarf varieties of wheat are widely used in North America due to both reduced potential for lodging and high yields. Dwarf fruit trees are also extensively used and allow farmers to produce more fruit per acre thereby increasing economic yield potential. There are other benefits that may be realized from the use of dwarf crop plants and dwarf fruit trees including reductions in the amounts of pesticides and fertilizers required, higher planting densities and reduced labor costs.

In view of the current trends of both increasing human population and the decreasing land area suitable for agriculture, increasing agricultural productivity is, and will continue to be, a challenge of paramount importance. Dwarf crop plants and fruit trees have been and will continue to be important components of our agricultural production system. Increased usage of dwarf crop plants and dwarf fruit trees may help to meet the agricultural production demands of the future. However, commercially acceptable dwarf varieties are not available for all crops.

In addition to the use of dwarf plants to control plant height, synthetic chemicals are routinely applied to certain economically important plant species to reduce growth. Plant growth regulators known as growth retardants are used to reduce stem elongation in a variety of crops including cotton, grape vines, fruit trees, peanuts, wheat and ornamentals such as azaleas, chrysanthemums, hydrangeas, poinsettias and many bedding plants. All of the commonly used growth retardants are inhibitors of gibberellin biosynthesis and limit stem or shoot growth by reducing elongation. In the United States, the most widely used growth retardant is mepiquat chloride, which is registered for use on cotton. Benefits attributed to the use of mepiquat chloride on cotton include increased yield, improved defoliation, improved stress tolerance, more uniform crop maturity and the ability to harvest earlier. Previously, the growth retardant daminozide was registered for use in the United States on apples, grapes and peanuts under the trademarks ALAR and KYLAR but was removed from use on food crops due to human health concerns. Despite the demands of agricultural producers for a product to replace diaminozide, there are no growth retardants registered for use on grapes, fruit trees and peanuts in the United States. Daminozide, however, is still widely used on certain non-food, plant species.

Uncovering the molecular mechanisms that control plant growth processes such as cell division and cell elongation will likely aid in the development of new plant varieties with reduced stature and new methods for reducing plant growth. Such new plant varieties and methods may provide both farmers and horticulturists with environmentally benign alternatives to the use of synthetic growth-retarding chemicals.

Elongation of plant cells and organs is one of the most critical parameters of plant growth and development. Regulation of this trait in plants, however, is a fairly complicated process, as both external and internal factors influence it. The most important external stimulus is light, with its normally repressible or negative effect on cell elongation (Quail, P. H. (1995) *Science* 268:675–680; Kende et al. (1997) *Plant Cell* 9:1197–1210). The internal control of cell elongation is mediated by a number of chemicals, normally referred to as plant growth regulators or hormones (Kende et al. (1997) *Plant Cell* 9:1197–1210). Among the classical plant hormones, auxins and gibberellins (GAs) both promote cell elongation whereas cytokinins and abscisic acid each have been shown to have a negative effect on cell elongation (Kende et al. (1997) *Plant Cell* 9:1197–1210). Recently, another class of plant growth regulators, named brassinosteroids, has been identified that also dramatically promote plant growth (Yokota, T. (1997) *Trends Plant Sci.* 2:137–143; Azpiroz et al. (1998) *Plant Cell* 10:219–230; Choe et al. (1998) *Plant Cell* 10:231–243). However, the mechanisms by which plant hormones act, either singly or in concert, to control cell elongation remains unclear.

One way to gain an understanding of mechanisms that mediate cell elongation is to study mutants in which this aspect of plant growth is compromised (Klec et al. (1991) *Annu. Rev. Plant Physiol. Plant Mol. Biol.* 42:529–551). Numerous such mutants have been identified across most plant species, including maize, in which more than 25 single-gene mutations that affect plant stature have been characterized (Coe et al. (1988) In: *Corn & Corn Improvement*, G. F. Sprague (Ed.) Madison, Wis.; Sheridan, W. F. (1988) *Annu. Rev. Genet.* 22:353–385). These dwarf mutants are considered to be GA related, mainly because GA is the only phytohormone whose role in regulating height in maize has been convincingly established (Phinney et al. (1985) *Curr. Top. Plant Biochem. Physiol.* 4:67–74; Fujioka et al. (1988) *Proc. Natl. Acad. Sci. USA* 85:9031–9035). Both types of mutants, GA responsive and GA non-responsive, have been found in this collection of maize mutants. While genes for a number of GA-responsive mutants have been cloned and found to be involved in GA biosynthesis (Bensen et al. (1995) *Plant Cell* 7:75–84; Winkler et al. (1995) *Plant Cell* 7:1307–1317), nothing is known about the nature of defects in GA non-responsive maize mutants.

One type of GA non-responsive dwarf mutants that have received much attention from maize geneticists and breeders is called brachytic. These dwarfs are characterized by intemodes of substantially reduced length, relative to wild-type, without having any effect on the size or number of other organs, including the leaves, ear and tassel (Kempton, J. H. (1920) *J. Hered.* 11:111–115). There are three known brachytic mutations in maize, br1, br2 and br3, all of which are recessive (Coe et al. (1988) In: *Corn & Corn Improvement*, G. F. Sprague (Ed.) Madison, Wis.; Sheridan, W. F. (1988) *Annu. Rev. Genet.* 22:353–385). Because of the commercial interest in br2 for enhancing plant productivity (Pendleton et al. (1961) *Crop Sci.* 1:433–435; Duvick, D. N. (1977) *Maydica* 22:187–196; Djisbar et al. (1987) *Maydica* 32:107–123; Russel, W. A. (1991) *Adv. Agron.* 46:245–298), this dwarf has been characterized the most. Depending on the genetic background, plants homozygous recessive for br2 are 30–70% shorter than their normal sibs. This reduction in plant height is exclusively due to a reduction of the length of stalk (stem) internodes. In addition to being dwarf, br2 mutants grown under greenhouse conditions often suffer from buggy whip, a disease-like condition in which the unfurling leaves in the whorl undergo necrosis and stay stuck together. This condition often results in the death of the growing tip of the plant.

Although the dwarfing trait in maize has been extensively studied both genetically and molecularly, it has yet to be exploited successfully in breeding efforts in this crop plant. In contrast, dwarf mutants of sorghum have contributed significantly to the development of modern day cultivars. Sorghum and maize are both members of the grass (Poaceae or Gramineae) family and thus share many characteristics including genomic organization and plant body form. Out of the four dwarfing mutations exploited in sorghum, dw3, whose dwarfing phenotype looks very similar to that of br2 in maize, appears to be the most prominent. However, the only dw3 allele (dw3-ref) available thus far has a serious problem which limits its agronomic value. The dwarf phenotype associated with the dw3 allele is unstable, with a reversion frequency to wild-type (tall) as high as about 1% in certain genetic backgrounds. The instability of this dwarf phenotype, the mechanism of which has eluded sorghum geneticists thus far, not only continues to embarrass sorghum breeders, but also sometimes leads to the rejection of an otherwise promising inbred or hybrid.

To keep up with the demand for increased agricultural production, new targets are needed for genetically engineering agricultural plants for the improvement of agronomic characteristics. Elucidating the molecular mechanisms of cell division and elongation will provide new targets for agricultural scientists to manipulate.

SUMMARY OF THE INVENTION

Compositions and methods for expressing genes encoding P-glycoproteins in plants are provided. The compositions comprise nucleotide sequences encoding P-glycoproteins, particularly P-glycoproteins that control plant growth. The compositions further comprise nucleotide sequences of the Dw3 gene of sorghum. The sequences of the invention are useful in transforming plants for tissue-preferred or constitutive expression of P-glycoproteins and for isolating homologous nucleotide molecules that encode P-glycoproteins. Such sequences find use in methods for controlling the growth of organisms, particularly stem growth in plants. The sequences of the invention also find use in methods of enhancing the resistance of plants to pathogens.

The invention further encompasses methods for isolating nucleotide molecules that are capable of controlling the growth of plants. Such methods find use in the isolation of genes involved in plant growth processes.

Methods are provided for identifying plants that possess a mutant allele that is capable of conferring a stable mutant phenotype on an organism. Such methods find use in agriculture, particularly in the breeding of dwarf crop plants, particularly dwarf sorghum plants.

Expression cassettes comprising the sequences of the invention are provided. Additionally provided are transformed plants, plant tissues, plant cells and seeds thereof. Isolated proteins encoded by the nucleotide sequences of the invention are provided.

DETAILED DESCRIPTION OF THE INVENTION

The present invention is drawn to compositions and methods for manipulating the growth of organisms. The methods involve transforming organisms with nucleotide sequences encoding P-glycoproteins. In particular, the nucleotide sequences are useful for controlling stem growth in plants. Thus, transformed plants, plant cells, plant tissues and seeds are provided. Compositions are nucleic acids and proteins relating to P-glycoprotein or P-glycoprotein-like genes in plants. More particularly, nucleotide sequences of the Dw3 gene of sorghum and the amino acid sequences of the proteins encoded thereby are disclosed. The sequences find use in the construction of expression vectors for subsequent transformation into plants of interest, as probes for the isolation of other P-glycoprotein-like genes, as molecular markers, and the like.

The present invention discloses the first unequivocal evidence of the involvement of multidrug-resistance-like P-glycoproteins in the control of growth and development in an organism. Thus, it is recognized that any P-glycoprotein known in the art that affects growth and development can be used in the practice of the invention. For example, five other plant P-glycoproteins are known. See, for example Dudler et al. (1998) *Methods Enzym.* 292:162–173 (Arabidopsis), Davies et al. (1997) *Gene* 199:195–202 (Barley), Wang et al. (1996) *Plant Mol. Biol.* 31:683–687 (Potato) and GenBank Acession Numbers Y10227 and Y15990 (both from Arabidopsis); herein incorporated by reference. These and other P-glycoprotein sequences may be tested for an effect on growth by methods such as, for example, transformation with antisense sequences and monitoring effects on progeny plants.

The present invention also discloses methods for identifying genes encoding multidrug-resistance-like P-glycoproteins that control the growth of an organism, particularly a plant. An example of the identification of such a gene is disclosed for the Dw3 gene of sorghum. Also provided is a method for identifying an allele of a gene wherein the allele confers a stable dwarf phenotype on a plant. An embodiment of this method involves identifying stable mutant alleles of the Dw3 gene that confer a dwarf phenotype on sorghum plants.

Compositions of the invention include the native nucleotide sequences for P-glycoprotein genes, antisense sequences, as well as variants and fragments thereof. Particularly, the P-glycoprotein gene of the sorghum Dw3 locus and the respective amino acid sequence for the P-glycoproteins encoded thereby, as well as fragments and variants thereof are provided. The Dw3 nucleotide sequences are set forth in SEQ ID NOS: 1–3 and 7–8. The nucleotide sequences or corresponding antisense sequences find use in modulating the expression of a P-glycoprotein in a plant or plant cell. That is, the coding sequences can be used to increase the expression while antisense sequences can be used to decrease expression.

The sequences of the invention find use in methods of modifying the growth of an organism. In an embodiment of the invention, nucleotide sequences of the invention find use in methods of modifying plant growth. Toward this end, the sequences of the invention may be utilized in expression cassettes or nucleotide constructs operably linked to any one of a variety of plant promoters. Aspects of plant growth that may be impacted by the methods of the invention include, but are not limited to, plant height; the size, shape and number of cells and organs; cell division rate; cell elongation rate; the growth rate of the plant, its organs, tissues and cells; timing and location of organ initiation; life span; and the like.

The invention discloses methods for reducing plant growth which find use as alternatives to applying synthetic, growth-retarding chemicals to plants. These methods provide environmentally safe alternatives to traditional means of retarding stem elongation or growth with synthetic chemicals. Some embodiments of the invention make use of plants transformed with tissue-preferred promoters, particularly stem-preferred promoters, operably linked to nucleotide sequences encoding P-glycoproteins.

Methods are provided for reducing the growth of a plant. Such methods involve transforming plants with at least one nucleotide sequence of the invention. The nucleotide sequences may be used in either the sense or antisense orientation to suppress the level of an endogenous P-glycoprotein that controls the growth of a plant. By reducing the level in a plant of such a P-glycoprotein, particularly one that controls stem or stalk growth, a plant of reduced stature, a dwarf plant, may be achieved. Dwarf plants having improved agronomic characteristics can be obtained by these methods. Such improved agronomic characteristics include, but are not limited to, reduced potential for lodging, increased water-use efficiency, reduced life cycle, increased harvest efficiency and increased yield per unit area. The methods of the invention can eliminate the need to graft shoots of fruit trees on dwarfing rootstocks to produce dwarf fruit trees.

The methods of the invention find use in producing dwarf varieties of crop plants. In one embodiment of the invention, a dwarf Basmati rice plant is produced by transforming the plant with a nucleotide sequence encoding at least a portion of a P-glycoprotein that controls the growth of a plant. Basmati rice, known for its aromatic fragrance, slender, elongated grains, and relatively short cooking time, is the favorite type of rice of the majority of people in the Indian sub-continent. While commercially acceptable dwarf cultivars have been developed for other types of rice, previous attempts to produce commercially acceptable varieties of Basmati rice by traditional plant breeding methods have failed. While dwarf plants were obtained in such attempts, some of the distinctive grain characteristics that consumers expect in Basmati rice were not retained in the dwarf plants. The methods of the invention provide a means of making dwarf Basmati rice plants that produce grain possessing the characteristics desired by consumers.

The desired dwarf Basmati rice plants are produced by transforming a non-dwarf Basmati rice plant with a nucleotide sequence of the invention operably linked to a promoter that drives expression in a plant. While the choice of promoter depends on the desired outcome, the preferred promoters are tissue-preferred promoters, particularly stem-preferred promoters. Through cosuppression (sense suppression) or antisense suppression, such plants produce reduced levels of at least one P-glycoprotein that controls the growth of the Basmati rice plant, particularly stem growth. Preferably, the nucleotide sequence encodes at least a portion of a P-glycoprotein that controls the growth of a plant. More preferably, the nucleotide sequence is selected from the group consisting of SEQ ID NOS: 1–3 and 7–8 or a nucleotide sequence that encodes the amino acid sequence set forth in SEQ ID NOS: 4 or 9. Most preferably, the nucleotide sequence is from a rice gene that is homologous to the sorghum gene, Dw3. Such a rice gene encodes a P-glycoprotein that that controls the growth of the stem of the rice plant. The methods of the invention comprise transforming plants with the full-length nucleotide sequences of the invention, or any fragment or part thereof.

Methods for enhancing the resistance of plants to pathogens are provided. It is recognized that P-glycoproteins are involved in resistance mechanisms against pathogens. A mutant strain of the nematode, *Caenorhabditis elegans*, with deletions of two P-glycoprotein genes is substantially more susceptible to death than wild-type nematodes, when placed on a lawn of a *Pseudomonas aeruginosa* strain that is a pathogen of both plants and animals (Mahajan-Miklos et al. (1999) *Cell* 96:47–56). Br2 is a maize gene that encodes a multidrug-resistance-like P-glycoprotein that controls plant growth, particularly stem growth (See U.S. Provisional Application Serial No. 60/164,886 entitled "Genes and Methods for Manipulation of Growth" filed Nov. 12, 1999; herein incorporated by reference). Maize plants that are homozygous for the mutant allele, br2, display a dwarf stature, and under certain cultural conditions, can also display a phenotype known as "buggy whip" which mimics a bacterial pathogen-induced necrosis of the growing tip of a plant.

The methods for the enhancing resistance of plants to pathogens comprise transforming plants with the nucleotide sequences of the invention operably linked to promoters that drive expression in a plant. Such plants display enhanced resistance to pathogens, including bacteria, fungi, viruses, nematodes and insects. The methods find use in agriculture for limiting the impact of plant pathogens on crop production and provide an alternative to the use of synthetic pesticides in controlling plant pathogens.

Also provided are methods for identifying a plant with a stable mutant phenotype. Such methods find use in agriculture, particularly in the development of improved crop plants. The methods relate to an insertion-induced, mutant phenotype. By "insertion-induced, mutant phenotype" is intended a mutant phenotype that is due to the insertion of a nucleotide, or a sequence of nucleotides, into the sequence of a gene of interest. While the invention does not depend upon a particular genetic mechanism for such an insertion-induced mutant phenotype, the presence of such an insertion within a gene typically disrupts the normal wild-type function of the gene, or gene product thereof. While the methods of the invention are not bound by any particular type of insertion, such an insertion may be due to, for example, the insertion of a transposon or transposable element, or the duplication of a nucleotide sequence such as those which are known to occur as a result of genetic recombination.

Preferably, such an insertion-induced phenotype is unstable from one generation to the next. That is, self pollination of one or more like plants having the insertion-induced phenotype results in at least one individual from among the resulting progeny population that has reverted to the wild-type phenotype. More preferably, such phenotypic instability, from one generation to the next, is due to the loss of at least a portion of the insertion from the gene of interest and that such a loss results in at least one progeny plant, which has reverted to a wild-type phenotype. The methods of the present invention involve identifying an individual with a stable mutant phenotype from among such progeny population.

To identify a plant possessing an allele of a gene that confers a stable mutant phenotype, genomic DNA from a mutant plant is analyzed to determine if at least one copy of the gene of interest lacks the insertion, or at least a portion thereof. Generally, the mutant plant is selected from a population of progeny derived from the self pollination of one or more plants having the insertion-induced, mutant phenotype. Typically, in a population of such progeny, wild-type revertants will also be observed, indicating that at least a portion of the insertion has excised from the gene of interest. The genomic DNA of the selected mutant plant can be isolated and analyzed for the absence of all or a portion of the insertion by techniques known to those of ordinary skill in the art such as, for example, Southern blotting, restriction fragment length polymorphism (RFLP) analysis and DNA amplification by polymerase chain reaction (PCR). Once a mutant plant lacking a portion of the insertion is identified, the progeny of such a mutant plant can be monitored to verify phenotypic stability. If desired, subsequent generations can also be monitored.

Also provided are plants having stable mutant phenotypes and nucleotide sequences of alleles of genes which are capable of conferring a stable mutant phenotype on a plant.

A method of the invention involves identifying a sorghum plant with a stable dwarf phenotype. Such a sorghum plant possesses in its genome a stable mutant allele of the Dw3 gene. Such a stable mutant allele is capable of conferring a stable dwarf phenotype on a sorghum plant and the nucleotide sequence of a fragment of such an allele is set forth in SEQ ID NO: 2. One method of the invention employs RFLP analysis utilizing Southern blotting with a probe derived from nucleotide sequences of maize Br2. This method additionally involves PCR amplification and DNA sequence analysis to determine the nucleotide sequence of the stable mutant allele.

Methods are provided for identifying nucleotide sequences encoding gene products that control plant growth. Such gene products, like the DW3 protein, impact or modify the growth of a plant in detectable way by, for example, affecting characteristics such as the height or shape of a cell, organ or the plant body itself, cell number, cell division rate or cell elongation rate, organ growth rate, appearance of reproductive structures, timing and location of organ initiation and the like. The methods of the invention are particularly directed toward nucleotide sequences which influence the height or stature of a plant. The nucleotide sequences of the invention find use in any method known to those skilled in the art for identifying homologous sequences. Such methods for identifying homologous sequences include PCR amplification, hybridization, Southern blotting, colony hybridization and the like.

An embodiment of the invention involves the use of PCR amplification to identify nucleotide sequences encoding gene products that control plant growth. Such PCR amplification comprises the use of at least one oligonucleotide primer derived from a nucleotide sequence encoding of a gene encoding a multidrug-resistance-like P-glycoprotein. Preferably, such a nucleotide sequence is from a gene that encodes a P-glycoprotein that controls the growth of an organism, particularly a plant. More preferably, the nucleotide sequence is selected from the group consisting of SEQ ID NOS: 1–3 and 7–8.

In another embodiment, oligonucleotide primers (SEQ ID NOS: 5–6) were prepared from the sequences of Br2. Such primers were used to PCR amplify Dw3 from genomic DNA isolated from sorghum plants. Following DNA sequencing the identity of Dw3 was revealed. In a similar manner, other homologues of both Br2 and Dw3 can be identified using the same primers or other primers derived from any gene encoding a P-glycoprotein that controls the growth of an organism.

In still another exemplary embodiment of the invention, one or more nucleotide sequences set forth in SEQ ID NOS: 1–3 and 5–8 or a nucleotide sequence encoding the amino acid sequence set forth in SEQ ID. NO. 4 or 9 are used to design hybridization probes or PCR primers to identify a gene in the genome of a Basmati rice plant that is homologous to the sorghum gene, Dw3. Preferably, such a gene, from a Basmati rice plant, encodes a P-glycoprotein. More preferably, such a gene encodes a P-glycoprotein that controls the growth of the Basmati rice plant. Most preferably, such a gene encodes a P-glycoprotein that controls the stem growth of the Basmati rice plant.

The P-glycoproteins of the invention encompass all polypeptides and nucleotide sequences encoding them that share substantial sequence identity to the sequences of the invention whether or not such polypeptides possess covalently attached carbohydrates or carbohydrate-containing chains.

By "control growth of an organism" is intended to include impacting, modifying, modulating, affecting, increasing, and decreasing growth and growth-related processes of an organism. Such processes may influence any of a multitude of characteristics of an organism including, but not limited to, cell size and shape, organism size and shape, cell division rate, cell enlargement rate, organ growth rate, onset of reproductive maturity and life span.

By "mutant phenotype" is intended any non-wild-type, non-typical or non-standard phenotype which occurs as a result of a genetic alteration in the genome of an organism. When used in reference to domesticated plants and animals, a "mutant phenotype" is any phenotype that is substantially different from the typical phenotype of the particular domesticated breed or cultivated variety from which the mutant phenotype arose.

By "mutant plant" is intended a plant having a mutant phenotype.

By "mutant allele" is intended an allele of a gene that is capable of causing a "mutant phenotype."

By "dwarf" is intended atypically small. By "dwarf plant" is intended an atypically small plant. Generally, such a "dwarf plant" has a stature or height that is reduced from that of a typical plant by about 5%, 10%, 15%, 20%, 25%, 30%, 35%, 40%, 45%, 50%, 55%, 60% or greater. Generally, but not exclusively, such a dwarf plant is characterized by a reduced stem, stalk or trunk length when compared to the typical plant.

By "nucleotide molecule" is intended a molecule composed of nucleotides covalently bound to one another. Nucleotides include both ribonucleotides and deoxyribonucleotides. "Nucleotide molecule" encompasses single-stranded and double stranded forms of both DNA and RNA. "Nucleotide molecules" may be naturally occurring, synthetic or a combination of both. The linear arrangement of nucleotides in a "nucleotide molecule" is referred to as a "nucleotide sequence" and unless specified otherwise is presented herein from left to right corresponding to 5'-to-3' direction. Because of the complementary nature of the opposite strands of a double-stranded nucleotide molecule, a nucleotide sequence of the invention additionally encompasses its complementary antisense sequence.

Compositions of the invention include native nucleotide sequences for genes encoding multidrug-resistance-like-gene-encoded P-glycoproteins, homologues of multidrug-resistance-like-gene-encoded P-glycoproteins, antisense sequences, as well as fragments and variants and fragments thereof. In particular, the present invention provides for isolated nucleic acid molecules comprising nucleotide sequences encoding the amino acid sequences shown in SEQ ID NOS: 4 and 9, or the nucleotide sequences encoding the DNA sequences deposited in a bacterial host as Patent Deposit No. PTA 2645. Further provided are polypeptides having an amino acid sequence encoded by a nucleic acid molecule described herein, for example those set forth in SEQ ID NOS: 3 and 8, respectively, those deposited in a bacterial host as Patent Deposit Nos. PTA 2645, and fragments and variants thereof.

Plasmids containing the nucleotide sequences of the invention were deposited with the Patent Depository of the American Type Culture Collection (ATCC), Manassas, Va., on Nov. 1, 2000 and assigned Patent Deposit No PTA 2645. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain biological activity of the native P-glycoprotein and hence retain one or more functions of the native P-glycoprotein such as, for example, transmembrane transporter activity and ATP binding. Alternatively, fragments of a nucleotide sequence that are useful as hybridization probes may or may not encode protein fragments retaining biological activity. Thus, fragments of a nucleotide sequence may range from at least about 20 nucleotides, about 50 nucleotides, about 100 nucleotides, and up to the full-length nucleotide sequence of the invention.

A fragment of a P-glycoprotein gene nucleotide sequence that encodes a biologically active portion of a P-glycoprotein of the invention will encode at least 15, 20, 25, 30, 50, 75, 100, 150, 200, 250, 300, 350, 400, 450, 500, 550, 600, 650, 700, 800, 900, 1,000, 1,100, 1,200, 1,300, or 1,400 contiguous amino acids, or up to the total number of amino acids present in a full-length P-glycoprotein of the invention (for example, 415 and 1,421 amino acids for SEQ ID NOS: 4 and 9). Fragments of a P-glycoprotein gene nucleotide sequence that are useful as hybridization probes for PCR primers generally need not encode a biologically active portion of a P-glycoprotein.

Thus, a fragment of a P-glycoprotein gene nucleotide sequence may encode a biologically active portion of a P-glycoprotein, or it may be a fragment that can be used as a hybridization probe or PCR primer using methods disclosed below. A biologically active portion of a P-glycoprotein can be prepared by isolating a portion of one of the P-glycoprotein gene nucleotide sequences of the invention, expressing the encoded portion of the P-glycoprotein e.g., by recombinant expression in vitro), and assessing the activity of the portion of the P-glycoprotein. Nucleic acid molecules that are fragments of a P-glycoprotein gene nucleotide sequence comprise at least 16, 20, 50, 75, 100, 150, 200, 300, 500, 700, 1,000, 1,200, 1,500, 2,000, 2,500, 3,000, 3,500, 4,000, 4,500, 5,000, 5,500, 6,000 nucleotides, or up to the number of nucleotides present in a full-length P-glycoprotein nucleotide sequence disclosed herein (for example, 2,139, 1,267, 1,261, 6,827, and 4213 nucleotides for SEQ ID NOS: 1–3, and 7–8, respectively).

By "variants" is intended substantially similar sequences. For nucleotide sequences, conservative variants include those sequences that, because of the degeneracy of the genetic code, encode the amino acid sequence of one of the P-glycoprotein polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a P-glycoprotein protein of the invention. Generally, variants of a particular nucleotide sequence of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, transporter activity or ATP binding activity as described herein. Such variants may result from, for example, genetic polymorphism or from human manipulation. Biologically active variants of a native P-glycoprotein of the invention will have at least about 40%, 50%, 60%, 65%, 70%, generally at least about 75%, 80%, 85%, preferably at least about 90%, 91%, 92%, 93%, 94%, 95%, 96%, 97, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the P-glycoproteins can be prepared by mutations in the DNA. Methods for mutagenesis and nucleotide sequence alterations are well known in the art. See, for example, Kunkel (1985) *Proc. Natl. Acad. Sci. USA* 82:488492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired transporter activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays.

Variant nucleotide sequences and proteins also encompass nucleotide sequences and proteins derived from a mutagenic and recombinogenic procedure such as DNA shuffling. With such a procedure, one or more different P-glycoprotein coding sequences can be manipulated to create a variant nucleotide sequence encoding a variant P-glycoprotein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the P-glycoprotein gene of the invention and other known P-glycoprotein genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad Sci USA* 91:10747–1075 1; Stemmer (1994) *Nature* 370:389–391; Crameri et al. (1997) *Nature Biotech*. 15:436–438; Moore et al. (1997) *J Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2nd ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}p$, or any other detectable marker. Thus, for example, probes for hybridization can be made by labeling synthetic oligonucleotides based on the P-glycoprotein gene nucleotide sequences of the invention. Methods for preparation of probes for hybridization and for construction of cDNA and genomic libraries are generally known in the art and are disclosed in Sambrook et al. (1989) *Molecular Cloning: A Laboratory Manual* (2nd ed., Cold Spring Harbor Laboratory Press, Plainview, N.Y.).

For example, the entire Dw3 sequence disclosed herein, or one or more portions thereof, may be used as a probe capable of specifically hybridizing to corresponding P-glycoprotein gene sequences and messenger RNAs. To achieve specific hybridization under a variety of conditions, such probes include sequences that are unique among P-glycoprotein gene sequences and are preferably at least about 10 nucleotides in length, and most preferably at least about 20 nucleotides in length. Such probes may be used to amplify corresponding P-glycoprotein gene sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2nd ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least two-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. The duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m$=81.5° C. +16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2nd ed., Cold Spring Harbor Laboratory Press, Plainview, N.Y.).

Thus, isolated sequences that encode for P-glycoproteins and which hybridize under stringent conditions to the to the P-glycoprotein gene sequences disclosed herein, or to fragments thereof, are encompassed by the present invention. Such sequences will be at least about 70% to 75%, about 80% to 85%, and even 90%, 91%, 92%, 93%, 94%, 95%, 96%, 97%, 98%, 99% or more homologous with the disclosed sequences. That is, the sequence identity of sequences may range, sharing at least about 70% to 75%, about 80% to 85%, and even at least about 75%, 80%, 85%, 90%, 91%, 92%, 93%, 94%, 95%, 96%, 97%, 98%, 99% or more sequence identity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) CABIOS 4:11–17; the local homology algorithm of Smith et al. (1981) Adv. Appl. Math. 2:482; the homology alignment algorithm of Needleman and Wunsch (1970) J. Mol. Biol. 48:443–453; the search-for-similarity-method of Pearson and Lipman (1988) Proc. Natl. Acad. Sci. 85:2444–2448; the algorithm of Karlin and Altschul (1990) Proc. Natl. Acad. Sci. USA 872264, modified as in Karlin and Altschul (1993) Proc. Natl. Acad. Sci. USA 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) Gene 73:237–244 (1988); Higgins et al. (1989) CABIOS 5:151–153; Corpet et al.

(1988) Nucleic Acids Res. 16:10881–90; Huang et al. (1992) CABIOS 8:155–65; and Pearson et al. (1994) Meth. Mol. Biol. 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) J. Mol. Biol. 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used.

Computer implemetations of these mathematical algorithms can be utilized for comparasion of sequences to determine sequence identity. Such implemetations included, but are not limited to: CLUSTAL in the PC/Gene program (available from intelligenetics. Mountain View, Calif.); the ALIGN program (Version 2.0) and GAP, BESTFIT, BALST, FASTA, and TFASTA in the Wisconsin Geneies Software Package, Version 8 (available from Genetics Computer Group (GCG), 575 Science Drive, Madison, Wis., USA). Alignments using these programs can be performed using the default parameters. The CLUSTAL program is well described by Higgins al. (1988) Gene 73:237–244 (1988); Higgin et al. (1989) CABIOS 5:151–153; Corpet et al. (1988) Nucleic Acids Res. 16:10881-90; Huang et al. (1992) CABIOS 8:155–65; and Pearson et al. (1994) Meth. Mol. Biol. 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) J. Mol. Biol. 215:403 are based on the algorithm of Karlin and Altschul (1990) supra BLAST nucleotide searches can be performed with the BLASTN program, score=100, wordlength=12, to obtain nucleotide sequences homologous to a nucleotide sequence encoding a protein of the invention invention. BLAST protein searches can be performed with the BLASTX program, score=50, wordlength=3, to obtain amino acid sequence homologous to a protein or polypeptide of the invention. To obtain gapped alignments for comparasion purposes, Gapped BLAST (in BLAST 2.0) can be utilized as described in Altschul at al. (1997) Nucleic Acids Res. 25:3389. Alternatively, PSI-BLAST (in BLAST 2.0) can be used to perform an iterated search that detects distant relationship between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See ncbi.hlm.nih.gov (a www prefix must be used). Alignment may also be performed manually by inspection.

Unless otherwise stated, sequence identity/similarity values provided herein refer to the value obtained using GAP Version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) J. Mol. Biol. 48: 443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) Proc. Natl. Acad. Sci. USA 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman et al. (1970) *J Mol. Biol.* 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

Furthermore, it is recognized that the methods of the invention may employ a nucleotide construct that is capable of directing, in a transformed plant, the expression of at least one protein, or at least one RNA, such as, for example, an antisense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or an RNA.

In addition, it is recognized that methods of the present invention do not depend on the incorporation into the genome of the entire nucleotide construct comprising a P-glycoprotein nucleotide sequence, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al.

(1999) *Proc. Natl. Acad Sci. USA* 96:8774–8778; herein incorporated by reference.

The invention encompasses the use of methods, such as, for example, chimeraplasty to alter P-glycoprotein genes in plants. Such alterations include, for example, changes in the coding sequence that alter the amino acid sequence of the P-glycoprotein encoded thereby, resulting in a reduction in, or loss of, the function of the P-glycoprotein encoded by that gene.

The P-glycoprotein nucleotide sequences of the invention are provided in expression cassettes for expression in the plant of interest. The cassette will include 5'-and 3'-regulatory sequences operably linked to a P-glycoprotein nucleotide sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the P-glycoprotein nucleotide sequence to be under the transcriptional regulation of the regulatory regions. The expression cassette may additionally contain selectable marker genes.

The expression cassette will include in the 5'-3' direction of transcription, a transcriptional and translational initiation region, a P-glycoprotein nucleotide sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced.

While it may be preferable to express the sequences using heterologous promoters, the native promoter sequences may be used. Such constructs would change expression levels of a P-glycoprotein in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acid Res.* 15:9627–9639.

Where appropriate, the gene(s) may be optimized for increased expression in the transformed plant. That is, the genes can be synthesized using plant-preferred codons for improved expression. Methods are available in the art for synthesizing plant-preferred genes. See, for example, U.S. Pat. Nos. 5,380,831, and 5,436,391, and Murray et al. (1989) *Nucleic Acids Res.* 17:477–498, herein incorporated by reference.

Additional sequence modifications are known to enhance gene expression in a cellular host These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5'-leader sequences in the expression cassette construct. Such leader sequences can act to enhance translation. Translation leaders are known in the art and include: picornavirus leaders, for example, EMCV leader (Encephalomyocarditis 5'-noncoding region) (Elroy-Stein el al. (1989) *PNAS USA* 86:6126–6130); potyvirus leaders, for example, TEV leader (Tobacco Etch Virus) (Allison et al. (1986); MDMV leader (Maize Dwarf Mosaic Virus); *Virology* 154:9–20), and human immunoglobulin heavy-chain binding protein (BiP), (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, N.Y.), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

It is recognized that with the nucleotide sequences of the invention, antisense constructions, complementary to at least a portion of the messenger RNA (mRNA) for the P-glycoprotein gene sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding target sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation, also known as cosuppression methods, are known in the art. The methods generally involve transforming plants with a nucleotide construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) Curr. Opin. Biotech. 3:506–511; Christopherson et al. (1992) Proc. Natl. Acad. Sci. USA 89:6314–6318; Yao et al. (1992) Cell 71:63–72; Reznikoff (1992) Mol. Microbiol. 6:2419–2422; Barkley et al. (1980) in The Operon, pp. 177–220; Hu et al. (1987) Cell 48:555–566; Brown et al. (1987) Cell 49:603–612; Figge et al. (1988) Cell 52:713–722; Deuschle et al. (1989) Proc. Natl. Acad Aci. USA 86:5400–5404; Fuerst et al. (1989) Proc. Natl. Acad. Sci. USA 86:2549–2553; Deuschle el al. (1990) Science 248:480–483; Gossen (1993) Ph.D. Thesis, University of Heidelberg; Reines et al. (1993) Proc. Natl. Acad. Sci. USA 90:1917–1921; Labow et al. (1990) Mol. Cell. Biol. 10:3343–3356; Zambretti et al. (1992) Proc. Natl. Acad. Sci. USA 89:3952–3956; Baim et al. (1991) Proc. Natl. Acad Sci. USA 88:5072–5076; Wyborski et al. (1991) Nucleic Acids Res. 19:4647–4653; Hillenand-Wissman (1989) Topics Mol. Struc. Biol. 10:143–162; Degenkolb et al. (1991) Antimicrob. Agents Chemother. 35:1591–1595; Kleinschnidt et al. (1988) Biochemistry 27:1094–1104; Bonin (1993) Ph.D. Thesis, University of Heidelberg; Gossen et al. (1992) Proc. Natl. Acad. Sci USA 89:5547–5551; Oliva et al. (1992) Antimicrob. Agents Chemother. 36:913–919; Hlavka et al. (1985) Handbook of experimental Pharmacology, Vol. 78 (Springer-Verlag, Berlin); Gill et al. (1988) Nature 334:721–724. Such disclosures are herein incorporated by reference.

The above list of selectable marker genes is not meant to be limiting. Any selectable marker gene can be used in the present invention.

A number of promoters can be used in the practice of the invention. The promoters may be selected based on the desired timing, localization and level of expression of the P-glycoprotein genes in a plant. Constitutive, tissue-preferred, pathogen-inducible, wound-inducible and chemically regulatable promoters can be used in the practice of the invention.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810–812); rice actin (McElroy et al. (1990) Plant Cell 2:163–171); ubiquitin (Christensen et al. (1989) Plant Mol. Biol. 12:619–632 and Christensen et al. (1992) Plant Mol. Biol. 18:675–689); pEMU (Last et al. (1991) Theor. Appl. Genet. 81:581–588); MAS (Velten et al. (1984) EMBO J. 3:2723–2730); ALS promoter (U.S. application Ser. No. 08/409,297), and the like. Other constitutive promoters include, for example, U.S. Pat. Nos. 5,608,149; 5,608,144; 5,604,121; 5,569,597; 5,466,785; 5,399,680; 5,268,463; and 5,608,142.

Tissue-preferred promoters can be utilized to target enhanced P-glycoprotein expression within a particular plant tissue. Tissue-preferred promoters include Yamamoto et al. (1997) Plant J. 12(2):255–265; Kawamata et al. (1997) Plant Cell Physiol. 38(7):792–803; Hansen et al. (1997) Mol. Gen Genet. 254(3):337–343; Russell et al. (1997) Transgenic Res. 6(2):157–168; Rinehart et al. (1996) Plant Physiol. 112(3):1331–1341; Van Camp et al. (1996) Plant Physiol. 112(2):525–535; Canevascini et al. (1996) Plant Physiol. 112(2):513–524; Yamamoto et al. (1994) Plant Cell Physiol. 35(5):773–778; Lam (1994) Results Probl. Cell Differ. 20:181–196; Orozco et al. (1993) Plant Mol Biol. 23(6):1129–1138; Matsuoka et al. (1993) Proc Natl. Acad. Sci. USA 90(20):9586–9590; and Guevara-Garcia et al. (1993) Plant J. 4(3):495–505. Such promoters can be modified, if necessary, for weak expression.

Leaf-preferred promoters include, Yamamoto et al. (1997) Plant J. 12(2):255–265; Kawamata et al. (1997) Plant Cell Physiol. 38(7):792–803; Hansen et al. (1997) Mol. Gen. Genet. 254(3):337–343; Russell et al. (1997) Transgenic Res. 6(2): 157–168; Rinehart et al. (1996) Plant Physiol. 112(3):1331–1341; Van Camp et al. (1996) Plant Physiol. 112(2):525–535; Canevascini et al. (1996) Plant Physiol.. 112(2):513–524; Yamamoto et al. (1994) Plant Cell Physiol. 35(5):773–778; Lam (1994) Results Probl. Cell Differ. 20:181–196; Orozco et al. (1993) Plant Mol. Biol. 23(6):1129–1138; Matsuoka et al. (1993) Proc. Natl. Acad. Sci. USA 90(20):9586–9590; and Guevara-Garcia et al. (1993) Plant J. 4(3):495–505.

Root-preferred promoters are known and can be selected from the many available from the literature or isolated de novo from various compatible species. See, for example, Hire et al. (1992) Plant Mol. Biol. 20(2): 207–218 (soybean root-preferred glutamine synthetase gene); Keller and Baumgartner (1991) Plant Cell 3(10):1051–1061 (root-preferred control element in the GRP 1.8 gene of French bean); Sanger et al. (1990) Plant Mol. Biol. 14(3):433–443 (root-preferred promoter of the mannopine synthase (MAS) gene of Agrobacterium tumefaciens); and Miao et al. (1991) Plant Cell 3(1): 11–22 (full-length cDNA clone encoding cytdsolic glutamine synthetase (GS), which is expressed in roots and root nodules of soybean). See also Bogusz et al. (1990) Plant Cell 2(7):633–641, where two root-preferred promoters isolated from hemoglobin genes from the nitrogen-fixing nonlegume Parasponia andersonii and the related non-nitrogen-fixing nonlegume Trema tomentosa are described. The promoters of these genes were linked to a β-glucuronidase reporter gene and introduced into both the nonlegume Nicotiana tabacum and the legume Lotus corniculatus, and in both instances root-preferred promoter activity was preserved. Leach and Aoyagi (1991) describe their analysis of the promoters of the highly expressed roIC and rolD root-inducing genes of Agrobacterium rhizogenes (see Plant Science (Limerick) 79(1):69–76). They concluded that enhancer and tissue-preferred DNA determinants are dissociated in those promoters. Teeri et al. (1989) used gene fusion to lacZ to show that the Agrobacterium T-DNA gene encoding octopine synthase is especially active in the epidermis of the root tip and that the TR2' gene is root preferred in the intact plant and stimulated by wounding in leaf tissue, an especially desirable combination of characteristics for use with an insecticidal or larvicidal gene (see EMBO J. 8(2):343–350). The TR1' gene, fused to nptII (neomycin phosphotransferase II) showed similar characteristics. Additional root-preferred promoters include the VfENOD-GRP3 gene promoter (Kuster et al. (1995) Plant Mol. Biol. 29(4):759–772); and rolB promoter (Capana et al. (1 994) Plant Mol. Biol. 25(4):681–691. See also U.S. Pat. Nos. 5,837,876; 5,750,386; 5,633,363; 5,459,252; 5,401,836; 5,110,732; and 5,023,179.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *Plant Cell* 4:645–656; and Van Loon (1985) *Plant Mol. Viro.* 4:111–116. See also the copending applications entitled "Inducible Maize Promoters", U.S. application Ser. No. 60/076,100, filed Feb. 26, 1998, and U.S. application Ser. No. 60/079,648, filed Mar. 27, 1998, both of which are herein incorporated by reference.

Of interest are promoters that are expressed locally at or near the site of pathogen infection. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad Sci. USA* 83:2427–2430; Somsisch et al. (1988) *Mol. Gen. Genet.* 2:93–98; and Yang (1996) *Proc. Natl. Acad Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189–200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425–449; Duan et al. (1996) *Nature Biotechnology* 14:494–498); wun1 and wun2, U.S. Pat. No. 5,428,148; win1 and win2 (Stanford et al. (1989) *Mol. Gen. Genet.* 215:200–208); systemin (McGurl et al. (1992) *Science* 225:1570–1573); WIP1 (Rohmeier et al. (1993) *Plant Mol. Biol.* 22:783–792; Eckelkamp et al. (1993) *FEBS Letters* 323:73–76); MPI gene (Corderok et al. (1994) *Plant J.* 6(2):141–150); and the like, herein incorporated by reference.

Chemically regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemically inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemically regulated promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters (see, for example, Gatz et al. (1991) *Mol. Gen. Genet.* 227:229–237, and U.S. Pat. Nos. 5,814,618 and 5,789,156), herein incorporated by reference.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Biol/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

Alternatively, the nucleotide sequences of the invention can be introduced into an organism and allowed to undergo recombination with homologous regions of the organism's genome. Such homologous recombination approaches are well known to those of ordinary skill in the art and can be used to stably incorporate sequences of the invention into an organism. Further, such strategies can be used to introduce "knockout mutations" into a specific gene of an organism that shares substantial homology to the sequences of the invention. A knockout mutation is any mutation in the sequence of a gene that eliminates or substantially reduces the function or the level of the product encoded by the gene. Methods involving transformation of an organism followed by homologous recombination to stably integrate the sequences of the invention into the genome organism are encompassed by the invention. The invention is particularly directed to methods where sequences of the invention are utilized to alter the growth of an organism. Such methods encompass use of the sequences of the invention to interfere with the function or synthesis of a P-glycoprotein that controls growth of an organism.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

The present invention may be used for transformation of any plant species, including, but not limited to, corn (*Zea mays*), Brassica sp. (e.g., *B. napus, B. rapa, B. juncea*), particularly those Brassica species useful as sources of seed oil, alfalfa (*Medicago saliva*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus Cucumis such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as lobloily pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, rice, corn, alfalfa, sunflower, Brassica, soybean, cotton, safflower, peanut, sorghum, wheat, millet, tobacco, etc.), more preferably corn, rice and sorghum plants.

The invention is drawn to compositions and methods for increasing the resistance of a plant to a pathogen. Accordingly, the compositions and methods are also useful in protecting plants against fungal pathogens, viruses, nematodes, insects, acarids and the like.

By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened. The methods of the invention can be utilized to protect plants from disease, particularly those diseases that are caused by plant pathogens.

By "antipathogenic compositions" is intended that the compositions of the invention have antipathogenic activity and thus are capable of suppressing, controlling, and/or killing the invading pathogenic organism. An antipathogenic composition of the invention will reduce the disease symptoms resulting from pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens.

Assays that measure antipathogenic activity are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing an antipathogenic polypeptide or having an antipathogenic composition applied to its surface shows a decrease in tissue necrosis (ie., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107–15111, herein incorporated by reference.

Furthermore, in vitro antipathogenic assays include, for example, the addition of varying concentrations of the antipathogenic composition to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888–1892, herein incorporated by reference). Additionally, microspectrophotometrical analysis can be used to measure the in vitro antipathogenic properties of a composition (Hu et al. (1997) *Plant Mol. Biol.* 34:949–959 and Cammue et al. (1992) *J. Biol. Chem.* 267: 2228–2233, both of which are herein incorporated by reference).

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Scierotium rolfsii, Cercospora kikuchii, Cercospora sojina, Peronospora manshurica, Colletotrichum dematium*

(*Colletotichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata*, Soybean mosaic virus, *Glomerella glycines*, Tobacco Ring spot virus, Tobacco Streak virus, *Phakopsora pachyrhizi, Pythium aphanidermatum, Pythium ultimum, Pythium debaryanum*, Tomato spotted wilt virus, *Heterodera glycines Fusarium solani*; Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata*; Alfalfa: *Clavibater michiganese* subsp. *insidiosum, Pythium ultimum, Pythium irregulare, Pythium splendens, Pythium debaryanum, Pythium aphanidermatum, Phytophihora megasperma, Peronospora trifoliorum, Phoma medicaginis* var. *medicaginis, Cercospora medicaginis, Pseudopeziza medicaginis, Leptotrochila medicaginis, Fusarium, Xanthomonas campestris* p.v. *alfalfae, Aphanomyces euteiches, Stemphylium herbarum, Stemphylium alfalfae*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striformis, Pyrenophora triticirepentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum*, High Plains Virus, European wheat striate virus; Sunflower: *Plasmophora halstedii, Sclerotinia sclerotiorum*, Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Fusarium moniliforme* var. *subglutinans, Erwinia stewartii, Fusarium moniliforme, Gibberella zeae (Fusarium graminearum), Stenocarpella maydi (Diplodia maydis), Pythium irregulare, Pythium debaryanum, Pythium graminicola, Pythium splendens, Pythium ultimum, Pythium aphanidermatum, Aspergillusflavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella-maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride*, Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia carotovora*, Corn stunt *spiroplasma, Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium*, Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola (Glomerella graminicola), Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilianum (Sphacelotheca reiliana), Sphacelotheca cruenta, Sporisorium sorghi*, Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola*, etc.

Nematodes include parasitic nematodes such as root-knot, cyst, and lesion nematodes, including Heterodera and Globodera spp; particularly *Globodera rostochiensis* and *globodera pailida* (potato cyst nematodes); *Heterodera glycines* (soybean cyst nematode); *Heterodera schachtii* (beet cyst nematode); and *Heterodera avenae* (cereal cyst nematode).

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer; *Agrolis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; Melanotus spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, red legged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; Eleodes, Conoderus, and Aeolus spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper, *Melanoplus sanguinipes*, migratory grasshopper, *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodopiera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet arnyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcom maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rane: *Brevicoryne brassicae*, cabbage aphid; *Phyllotreta cruciferae*, Flea beetle; *Mamestra configurata*, Bertha armyworm; *Plutella xylostella*, Diamond-back moth; Delia ssp., Root maggots.

The following examples are offered by way of illustration and not by way of limitation.

EXAMPLE 1

Sorghum Dwarfing Gene, Dw3, Encodes a P-glycoprotein Homologue

It is well established that the sorghum dwarfing phenotype conferred by the dw3 recessive mutation is unstable, although the mechanism responsible for its instability remains unknown. The daw3 allele, referred to here as the reference allele (dw3-ref), reverts back to the wild-type form (conferring a tall phenotype) with a frequency of about 0.4% to about 1%. As a result, it is a commonplace to witness a number of tall sorghum plants in a field of dw3 dwarfs. To determine if there is any relationship between the maize br2 gene and the sorghum dw3 gene, leaf samples were collected from 8 dwarf and 8 tall (revertant) plants; these were expected to be true dw3 isogenics (identical throughout the genome except at the dw3 locus). The DNA of these samples was extracted, digested with PstI, and subjected to Southern blot analysis using a probe from the maize Br2 gene. A clear and consistent DNA polymorphism was observed between the tall and dwarf plants, with the restriction fragment from the revertant allele being about 1.0 kb smaller that the dw3-ref allele.

Two conclusions were made from this result. First, the sorghum Dw3 locus is structurally and functionally homologous to the maize Br2 gene, suggesting that they may turn out to be true orthologs (i.e., derived from the same ancestral gene by vertical descent). Second, since all revertants had the same RFLP pattern, and that the size of the revertant allele was smaller than the mutant allele, the mutable dw3-ref allele was probably caused by an insertion. To address the latter interpretation, sorghum DNA in the vicinity of the Br2-detected polymorphism was subjected to PCR amplification using two oligonucleotide primers (SEQ ID NOS: 5–6) derived from the nucleotide sequence of the maize Br2 gene.

PCR products were amplified from genomic DNA isolated from the tall revertants and dwarf plants with the dw3-ref allele. The PCR products were subsequently cloned and sequenced. The results obtained showed that a duplication of 882 bp had occurred in exon 5 of the dw3 gene that led to the generation of the dw3-refmutant allele (SEQ ID NO: 1). Thus, the dw3 dwarf phenotype in sorghum is likely due to an insertion-induced mutation that occurred within the Dw3 allele to give rise to the dw3-ref allele. A partial sequence of the tall revertant allele, designated Dw3-T is disclosed in SEQ ID NO: 3. The duplication present in the dw3-ref mutant allele also seems to be responsible for the unstable nature of dw3-ref. By an undetermined mechanism, this duplication is removed in tall revertants of dw3-ref.

Comparison of the partial amino acid sequence of the protein encoded by Dw3-T (SEQ ID NO: 4) revealed that, like BR2, this protein belongs to the family of multidrug-resistance-like P-glycoproteins. Whereas it shows more than 96% amino acid identity with the maize pgp1 (the Br2 gene), it exhibits 81% and 79% identity with P-glycoprotein genes of *Arabidopsis thaliana* and potato respectively.

Since the instability of the dw3-ref allele may result from some genetic recombination between two copies of the duplicated part of the gene, it might not always be precise. Some instances may occur where one or more extra base pairs may be left behind or deleted, leading in either case to a frame shift mutation. Such events are thus expected to generate new mutant alleles of dw3 that are devoid of the duplication. And since the duplication seems to be responsible for the instability of dw3-ref, the new mutant alleles of dw3 are expected to exhibit a stable dwarfing phenotype. Such stable dwarf alleles are highly desirable for breeding improved sorghum cultivars, as the instability of dw3 has been a constant nemesis for breeders for enhancing the production of sorghum.

To identify a stable dw3 allele, DNA was extracted from 200 dwarf sorghum plants and subjected to Southern blot analysis using a probe from the maize Br2 gene. Two dwarf plants were identified that exhibited a restriction pattern that was different from the rest of the dwarf plants. Genomic DNA was isolated from one of these two dwarf plants and amplified using the oligonucleotide primers (SEQ ID NOS: 5–6) as described supra. The PCR product was cloned and sequenced. Comparison of the nucleotide sequence of the cloned PCR product (SEQ ID NO: 2) from this dwarf plant to the sequence of dw3-ref(SEQ ID NO: 1) revealed that the duplication present in dw-3-ref was lost. Thus, this dwarf plant possesses a new dw3 allele, designated as dw3-1. Comparison of the nucleotide sequence of the dw3-1 allele with the Dw3-T allele demonstrated that the new dw3-1 allele has undergone minor changes.

To separate the new dw3-1 allele from the parental dw3-ref allele, the dwarf plant possessing the dw3-1 was self pollinated and seeds from plant were collected and planted. From the progeny, plants that were homozygous for dw3-1 were identified by Southern blot analysis, and the homozygous plants are being propagated to develop stable dwarfing gernplasm for sorghum. In addition, eight separate Pioneer proprietary sorghum inbreds are also being genotyped for the presence of new mutant derivatives of dw3-ref. The inbreds that were utilized are AGK1G, MK7G, MQC100G, ZYL24, YYU28W, CAJ14W, FYL14W, and YGC87W. They were selected on the basis of their reversion frequency, which was rated high, moderate or low. These inbreds were planted outdoors in Johnston, Iowa during the summer of 1999. Two hundred plants from each line were RFLP genotyped by digesting their DNA with PstI and hybridizing the resulting blots with a gene specific probe from the 3' end of the maize br2 gene. Four stable homozygous dwarf plants were identified from YYU28W and ten such plants were identified from FYL14W. Seeds from these stable dwarf plants have been harvested. The progeny of these stable dwarf plants can be used directly for the production of high-yielding sorghum hybrids with the desired stable dwarf phenotype.

EXAMPLE 2

Nucleotide Sequence of a Dw3 Gene that Encodes a Functional Gene Product

In order to clone the entire sequence from both the functional (Dw3) and the mutant (dw3-ref) alleles of the dw3 locus, a tall revertant plant and a dwarf sibling were selected from the inbred AGK1G. In this inbred line, tall plants appear at a frequency of 0.1–0.4%. The genotype of the tall revertant plant was expected to be heterozygous at the dw3 locus but otherwise identical to its dwarf sibling throughout the genome. To confirm that the tall revertant was heterozygous at the dw3 locus, DNA samples isolated from this plant and a number of dwarf siblings were characterized by Southern analysis using three probes representing the 5', middle and 3' parts of the maize br2 gene. As expected, polymorphism between dwarf siblings and the tall plant was localized only at the 3' end of dw3. This analysis allowed the identification of two EcoRI fragments from the tall revertant that when combined contained the entire Dw3 allele. These were a 14 kb EcoRI fragment that contained the 5' portion of the gene and an 8.1 kb fragment that contained the rest of the gene. A 9.0 kb fragment from the dw3-ref allele was determined to correspond to the 8.1 kb EcoRI fragment of the Dw3 allele. Three size-selected libraries (containing the 14 kb/EcoRI and 8.1 kb/EcoRI fragments from the tall revertant and the 9.0 kb/EcoRI fragment from the dwarf sibling) were constructed in Lambda cloning vectors of Stratagene. The 14.0 kb /EcoRI fragment library was constructed in λ Dash II and was screened with a probe coming from the extreme 5' end of the maize br2 gene. The other two libraries were prepared in λ ZapII and were screened with a probe from the 3' end of the maize br2 gene. Positive clones were isolated and λ DNA was extracted for each of these clones. The Dw3 and dw3 genes were PCR amplified into four overlapping 0.5 kb, 2.4 kb, 3.0 kb, and 1.3 kb fragments using gene specific primers and λ DNA as a template. These PCR fragments were cloned in TOPO vector (Invitrogen). From the dwarf dw3 clone of 9.0 kb, a unique 888 bp SacI fragment containing a part of the duplicated region was subcloned into pBSK+ vector (Stratagene).

DNA from at least two colonies of each PCR clone was sequenced using M13 forward, M13 reverse, and gene specific primers (GSPs). The 888 bp SacI fragment from the dw3-ref clone was sequenced by using T3 and T7 vector-specific primers alone. Sequence information, both from the extreme 5' and 3' ends of Dw3 and dw3 genes, was gathered by sequencing directly the λ DNA of both the 14.0 kb and 8.1 kb clones, using gene-specific primers. All of the sequence information was compiled and compared to reveal the cause of dwarfing in sorghum. A pairwise alignments between Dw3 and Br2 genes was done at the protein level by using Clustal W Program and at the nucleotide level by using BLAST Program of NCBL.

A polynucleotide of 6827 bp containing the fall length Dw3 gene was assembled and is presented in SEQ ID NO: 7. Structurally, the Dw3 gene has five exons and four introns. The length of five exons, from exon 1 through exon 5, is 616 bp, 537 bp, 326 bp, 230 bp, and 2400 bp, respectively. Intron 1 is 165 bp (nucleotides 639–803 of SEQ ID NO: 7); intron 2 is 110 bp (nucleotides 1441–1550); intron 3 is 846 bp (nucleotides 1877–2722); and intron 4 is 1471 bp (nucleotides 2953–4423) in length. The intron/exon boundaries of Dw3 are identical to that of the br2 gene of maize. The predicted Dw3-cDNA is 4209 bp long from the start codon to the end of the termination codon (SEQ ID NO: 8) and is thus 28 bp longer than the analogous region of the Br2-cDNA. Similarly, the predicted protein encoded by Dw3 is 1402 amino acids long (SEQ ID NO: 9), as compared to the 1394 amino acids predicted protein from Br2 gene. Multiple alignment results show that overall Dw3 is 92% and 91.8% identical to the maize Br2 gene at the nucleotide level and at the amino acid level, respectively.

PCR analysis of the polymorphic region between dw3 and br2 had earlier suggested that a duplication of a part of exon 5 resulted in the dw3-ref dwarfing allelle of sorghum. To address if it was exclusively the reason for the mutant nature of the dw3-ref allele, the sequence of the Dw3 allele from the tall revertant was compared with that of the dw3-ref allele. As shown previously, the difference was detected only in exon 5 between these alleles. In the mutant allele (dw3-ref, SEQ ID NO: 1), a stretch of 882 bp in exon 5 (from nucleotides 5650–6531 of SEQ ID NO: 7) is duplicated at the 6532 nucleotide position in the same direction. This duplication converted the 1312 bp PstI restriction fragment (from nucleotides 5463 bp to 6775 of SEQ ID NO: 7) in the functional Dw3 allele to the 2194 bp PstI fragment found in the dw3-ref allele, and thus was the cause for the polymorphism between these two alleles. Since no other changes were found between these alleles, the results clearly implicate this duplication as the sole cause for creating the dw3 dwarfing allele of sorghum. The addition of 882 bp to the cDNA will no doubt have a serious ramification for the structure and activity of the DW3 protein. These findings also show how the dw3-ref allele spontaneously corrects itself, every now and then, by getting rid of the duplication. The mechanism, by which this correction occurs, remains unknown, as does the mechanism by which the duplication occurred in the first place.

EXAMPLE 3

Transformation of Maize By Particle Bombardment and Regeneration of Transgenic Plants Immature maize embryos from greenhouse donor plants are bombarded with a plasmid containing a P-glycoprotein nucleotide sequence of the invention operably linked to a promoter that drives expression in a plant and the selectable marker gene PAT (Wohlleben et al. (1988) *Gene* 70:25–37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the P-glycoprotein nucleotide sequence of the invention operably linked to the plant promoter of interest is made. This plasmid DNA plus plasmid DNA containing a PAT selectable marker is precipitated onto 1.1 $\mu$m (average diameter) tungsten pellets using a $CaCl_2$ precipitation procedure as follows:

100 $\mu$l prepared tungsten particles in water

10 $\mu$l (1 $\mu$g) DNA in Tris EDTA buffer (1 $\mu$g total DNA)

100 $\mu$l 2.5 M $CaCl_2$

10 $\mu$l 0.1 M spermidine

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 $\mu$l 100% ethanol is added to the final tungsten particle pellet. For particle gun bombardment, the tungsten/DNA particles are briefly sonicated and 10 $\mu$l spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for dwarf phenotype or other phenotype associated with expression of the P-glycoprotein nucleotides sequence of the invention.

Bombardment and Culture Media

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialapbos(both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

EXAMPLE 4

Agrobacterium-Mediated Transformation of Maize and Regeneration of Transgenic Plants For Agrobacterium-mediated transformation of maize with a P-glycoprotein nucleotide sequence of the invention, preferably the method of Zhao is employed (U.S. Pat. No. 5,981,840, and PCT patent publication WO 098/32326; the contents of which are hereby incorporated by reference).

Briefly, immature embryos are isolated from maize and the embryos contacted with a suspension of Agrobacterium, where the bacteria are capable of transferring the P-glycoprotein nucleotide sequence of the invention to at least one cell of at least one of the immature embryos (step 1: the infection step). In this step the immature embryos are preferably immersed in an Agrobacterium suspension for the initiation of inoculation. The embryos are co-cultured for a time with the Agrobacterium (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of Agrobacterium without the addition of a selective agent for plant transform ants (step 3: resting step). Preferably the immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule comprising a nucleotide sequence selected from the group consisting of:
   (a) the nucleotide sequence set forth in SEQ ID NO: 7;
   (b) the nucleotide sequence set forth in SEQ ID NO: 8;
   (c) a nucleotide sequence encoding the amino acid sequence set forth in SEQ ID NO: 9; and,
   (d) a nucleotide sequence that is complemcentary to the nucleotide sequence of any one of (a)–(c).

2. An expression cassette comprising the nucleic acid molecule of claim 1, said nucleotide sequence operably linked to a promoter that drives expression in a plant cell.

3. The expression cassette of claim 2, wherein said promoter is selected from the group consisting of tissue-preferred, constitutive, chemically regulatable, and pathogen-inducible promoters.

4. A transformed plant having stably incorporated into its genome a nucleic acid molecule operably linked to a promoter that drives expression in a plant cell, wherein said nucleic acid molecule comprises a nucleotide sequence selected from the group consisting of:
   (a) the nucleotide sequence set forth in SEQ ID NO: 7;
   (b) the nucleotide sequence set forth in SEQ ID NO: 8;
   (c) a nucleotide sequence encoding the amino acid sequence set forth in SEQ ID NO: 9, and,
   (d) a nucleotide sequence that is complementary to the nucleotide sequence of any one of (a)–(c).

5. The plant of claim 4, wherein said promoter is selected from the group consisting of tissue-preferred, constitutive, chemically regulatable, and pathogen-inducible promoters.

6. The plant of claim 4, wherein said nucleic acid molecule is operably linked to said promoter in the antisense orientation.

7. The plant of claim 4, wherein said plant is a monocot.

8. The plant of claim 7, wherein said monocot is selected from the group consisting of maize, wheat, rice, sorghum, rye, millet and barley.

9. The plant of claim 4, wherein said plant is a dicot.

10. The plant of claim 9, wherein said dicot is selected from the group consisting of soybeans, sunflowers, safflowers, alfalfa, Brassica sp., cotton, peanuts and fruit trees.

11. Transformed seed of the plant of claim 4.

12. Transformed seed of the plant of claim 5.

13. Transformed seed of the plant of claim 6.

14. Transformed seed of the plant of claim 7.

15. Transformed seed of the plant of claim 8.

16. Transformed seed of the plant of claim 9.

17. Transformed seed of the plant of claim 10.

18. A method for modifying the growth of a plant, said method comprising transforming a plant with a nucleic acid molecule encoding a P-glycoprotein, said nucleic acid molecule operably linked a promoter that drives expression of said nucleic acid molecule in said plant, said nucleic acid molecule comprising a nucleotide sequence selected from the group consisting of:
   (a) the nucleotide sequence set forth in SEQ ID NO: 7;
   (b) the nucleotide sequence set forth in SEQ ID NO: 8;
   (c) a nucleotide sequence encoding the amino acid sequence set forth in SEQ ID NO: 9; and,
   (d) a nucleotide sequence that is complementary to the nucleotide sequence of any one of (a)–(c).

19. The method of claim 18, wherein said nucleic molecule is operably linked to said promoter in the antisense orientation.

20. The method of claim 18, wherein the height of said plant is reduced.

21. The method of claim 18, wherein said plant is a monocot.

22. The method of claim 18, wherein said monocot is selected from the group consisting of maize, wheat, rice, sorghum, rye, millet and barley.

23. A transformed plant cell having stably incorporated into its genome a nucleic acid molecule operably linked to a promoter that drives expression in a plant cell, wherein said nucleic acid molecule comprises a nucleotide sequence selected from the group consisting of:
   (a) the nucleotide sequence set forth in SEQ ID NO: 7;
   (b) the nucleotide sequence set forth in SEQ ID NO: 8;
   (c) a nucleotide sequence encoding the amino acid sequence set forth in SEQ ID NO: 9; and,
   (d) a nucleotide sequence that is complementary to the nucleotide sequence of any one of (a)–(c).

* * * * *